US007226732B2

(12) United States Patent
Sakai et al.

(10) Patent No.: US 7,226,732 B2
(45) Date of Patent: Jun. 5, 2007

(54) METHODS, APPARATUS, AND COMPUTER PROGRAMS FOR VERIFYING THE INTEGRITY OF A PROBE

(75) Inventors: Stanley H. Sakai, Cupertino, CA (US); William McMillan, Cupertino, CA (US)

(73) Assignee: Cepheid, Sunnyvale, CA (US)

( * ) Notice: Subject to any disclaimer, the term of this patent is extended or adjusted under 35 U.S.C. 154(b) by 676 days.

(21) Appl. No.: 09/906,897

(22) Filed: Jul. 16, 2001

(65) Prior Publication Data

US 2003/0064368 A1 Apr. 3, 2003

(51) Int. Cl.
*G01N 33/48* (2006.01)
*C12Q 1/68* (2006.01)
*C12P 19/34* (2006.01)

(52) U.S. Cl. ............................ 435/6; 435/91.2; 702/19

(58) Field of Classification Search .................... 435/6; 752/19

See application file for complete search history.

(56) References Cited

U.S. PATENT DOCUMENTS 5,863,736 A * 1/1999 Haaland ........................ 435/6
5,866,336 A * 2/1999 Nazarenko et al. ............ 435/6
6,174,670 B1 1/2001 Wittwer et al.
6,232,079 B1 5/2001 Wittwer et al.
6,312,929 B1 11/2001 McMillan

FOREIGN PATENT DOCUMENTS

WO WO 97/46707 A2 12/1997
WO WO 01/16367 A1 3/2001

OTHER PUBLICATIONS

Mallet et al. Journal of clinical Microbiology, vol. 33, No. 12, Dec. 1995, pp. 3201-3208.*

Livak et al., PCR Methods and Applications, vol. 4, pp. 357-362, 1995.*

Erlich H., PCR Technology, W. H. Freeman and Company, New York, pp. 24-25, 1992.*

Giesendorf et al., Clinical Chemistry, vol. 44, No. 3, pp. 482-486, 1998.*

Loffler et al. 16S rRNS Gene-Based Detection of Tetrachloroethene-Dechlorinating Desulfuromonas and Dehalococcoides Species. Applied and Environmental Microbiology, Apr. 2000, pp. 1369-1374.*

Wittwer et al., "A Microvolume Multisample Fluorimeter with Rapid Temperature Control", *Biotechniques* 22:1: 176-181 (1997).

Nitsche et al., "Different Real-Time PCR Formats Compared for the Quantitative Detection of Human Cytomegalovirus DNA", *Clinical Chemistry* 45:11: 1932-1937 (1999).

Roche Molecular Biochemicals: LightCycler Operator's Manual, version 3.5., pp. 1-190, (2000).

Pfaffl, "A new mathematical model for relative quantification in real-time RT-PCR", *Nucleic Acids Research* 29:9: 2002-2007 (2001).

Soong et al., "Quantitative Reverse Transcriptase-Polymerase Chain Reaction Detection of Cytokeratin 20 in Noncolorectal Lymph Nodes", *Clinical Cancer Research* 7: 3423-3429 (2001).

Li, Jianwei Jeffery et al.; "Using molecular beacons as a sensitive fluorescence assay for enzymatic cleavage of single-stranded DNA"; 2000, *Nucleic Acids Research*, vol. 28, No. 11, 5 pages.

Tyagi, Sanjay et al.; "Molecular Beacons: Probes that Fluoresce upon Hybridization"; 1996, *Nature Biotechnology*, vol. 14, pp. 303-308.

Vet, Jacqueline A.M. et al.; "Multiplex detection of four pathogenic retroviruses using molecular beacons"; 1999, *Proc. Natl. Acad. Sci.*, vol. 96, pp. 6394-6399.

Wittwer, Carl T. et al.; "Continuous Fluorescence Monitoring of Rapid Cycle DNA Amplification"; 1997, *BioTechniques*, vol. 22, No. 1, pp. 130-138.

* cited by examiner

*Primary Examiner*—John S. Brusca
*Assistant Examiner*—Russell S. Negin
(74) *Attorney, Agent, or Firm*—Townsend and Townsend and Crew LLP

(57) ABSTRACT

The present invention provides methods, apparatuses and computer programs for verifying the integrity of a probe by comparing the fluorescence value of a probe to a threshold value. The invention also provides for methods, apparatuses and computer programs for normalizing the fluorescence value of a probe and detecting a target nucleic acid in a sample.

89 Claims, 17 Drawing Sheets

```
         T T G
       A       C
     A           T
    A             C
    C             A
    G             A
    A             A
     C           A
      T         G
       C       A
        C G
        G C
        C G
        A T
        C G
FAM —— 5' C G 3' —— DABCYL
```

METHODS, APPARATUS, AND COMPUTER PROGRAMS FOR VERIFYING THE INTEGRITY OF A PROBE

BACKGROUND OF THE INVENTION

Methods for amplifying nucleic acids provide useful tools for the detection of human pathogens, detection of human genetic polymorphisms, detection of RNA and DNA sequences, for molecular cloning, sequencing of nucleic acids, and the like. In particular, the polymerase chain reaction (PCR) has become an important tool in the cloning of DNA sequences, forensics, paternity testing, pathogen identification, disease diagnosis, and other useful methods where the amplification of a nucleic acid sequence is desired. See e.g., *PCR Technology: Principles and Applications for DNA Amplification* (Erlich, ed., 1992); *PCR Protocols: A Guide to Methods and Applications* (Innis et al., eds, 1990).

PCR permits the copying, and resulting amplification, of a target nucleic acid. Briefly, a target nucleic acid, e.g. DNA, is combined with a sense and antisense primers, dNTPs, DNA polymerase and other reaction components. See Innis et al. The sense primer can anneal to the antisense strand of a DNA sequence of interest. The antisense primer can anneal to the sense strand of the DNA sequence, downstream of the location where the sense primer anneals to the DNA target. In the first round of amplification, the DNA polymerase extends the antisense and sense primers that are annealed to the target nucleic acid. The first strands are synthesized as long strands of indiscriminate length. In the second round of amplification, the antisense and sense primers anneal to the parent target nucleic acid and to the complementary sequences on the long strands. The DNA polymerase then extends the annealed primers to form strands of discrete length that are complementary to each other. The subsequent rounds serve to predominantly amplify the DNA molecules of the discrete length.

Hybridization probes are currently used to detect and quantify nucleic acids. Such probes are useful for hybridization assays, including in situ hybridization assays. Another use of these probes is to detect and quantify polynucleotide products from amplification reactions. There are many different types of assays that employ nucleic acid hybridization probes. Some of these probes generate signals with a change in the fluorescence of a fluorophore due to a change in its interaction with another molecule or moiety. Typically, the interaction is brought about by changing the distance between the fluorophore and the interacting molecule or moiety. These assays rely for signal generation on fluorescence resonance energy transfer, or "FRET." FRET utilizes a change in fluorescence caused by a change in the distance separating a first fluorophore from an interacting resonance energy acceptor, either another fluorophore or a quencher. Combinations of a fluorophore and an interacting molecule or moiety, including quenching molecules or moieties, are known as "FRET pairs." The mechanism of FRET-pair interaction requires that the absorption spectrum of one member of the pair overlaps the emission spectrum of the other member, the first fluorophore. If the interacting molecule or moiety is a quencher, its absorption spectrum must overlap the emission spectrum of the fluorophore. Stryer, L., *Ann. Rev. Biochem.* 1978, 47: 819–846; BIOPHYSICAL CHEMISTRY part II, Techniques for the Study of Biological Structure and Function, (C. R. Cantor and P. R. Schimmel, eds., 1980), pages 448–455, and Selvin, P. R., *Methods in Enzymology* 246: 300–335 (1995). Efficient, or a substantial degree of, FRET interaction requires that the absorption and emission spectra of the pair have a large degree of overlap. The efficiency of FRET interaction is linearly proportional to that overlap. Haugland, R. P., Yguerabide, Jr., and Stryer, L., *Proc. Natl. Acad. Sci. USA* 63: 24–30 (1969). Non-FRET probes have also been described. See, e.g., U.S. Pat. No. 6,150,097.

One method for detection of amplification products is the 5' nuclease PCR assay (also referred to as the TaqMan® assay) (Holland et al., *Proc. Natl. Acad. Sci. USA* 88: 7276–7280 (1991); Lee et al., *Nucleic Acids Res.* 21: 3761–3766 (1993)). This assay detects the accumulation of a specific PCR product by hybridization and cleavage of a doubly labeled fluorogenic probe (the "TaqMan®" probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "beacon probe" method described by Tyagi and Kramer (*Nature Biotech.* 14:303–309 (1996)), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in "open conformation," and fluorescence is detected, while those that remain unhybridized will not fluoresce (Tyagi and Kramer, *Nature Biotechnol.* 14: 303–306 (1996). As a result, the amount of fluorescence will increase as the amount of PCR product increases, and thus may be used as a measure of the progress of the PCR.

To be confident about the signal, or lack thereof, from a hybridization probe such as those described above, the user must control for the integrity of the probe. For example, where the fluorophore has been cleaved from the probe, or the polynucleotide body of the probe has been cleaved, fluorescence does not accurately reflect the quantity of probe binding a target. A typical control for the integrity of the probe involves a separate reaction mixture that contains a known amount of target. Thus, if the probe produces the appropriate signal for the known control sample, then it is assumed that the probe is intact. This technique has at least two drawbacks. First, it does not reflect the possibility that samples to be tested, unlike the control, have enzymes that could degrade the probes in the samples. Second, the technique requires the use of an additional reaction vessel. Thus, there remains a need for a fast and efficient method to determine the integrity of a hybridization probe directly in the test sample itself. The present invention addresses this and other problems.

SUMMARY OF THE INVENTION

The present invention provides methods of testing the integrity of at least one probe for the detection of a nucleic acid sequence. In some aspects, the methods comprise, (a) providing a mixture comprising at least one probe, which probe is capable of binding a nucleic acid;

(b) measuring a signal of the probe at one or more time point; and (c) determining the integrity of the probe by comparing the signal of the probe at the one or more time points with at least one threshold value.

In some aspects, the signal is fluorescence. In some aspects, the signal of the probe is measured when the probe is not bound to a target.

In some aspects, the probe is capable of hybridizing with a target nucleic acid molecule, the probe comprising a fluorophore and a quenching agent, wherein heating the probe causes the probe to change conformation from a first conformation to a second conformation, thereby changing the distance between the fluorophore and the quenching agent such that the fluorescence of the fluorophore is quenched or altered in the first conformation compared to the fluorescence of the fluorophore in the second conformation. In some embodiments, the signal of the probe is measured when the probe is not bound to the target nucleic acid molecule. In some embodiments, the fluorescence of the probe is measured at a temperature at or below the self-annealing temperature of the probe. In some embodiments, the fluorescence of the probe is measured at a temperature above the self-annealing temperature of the probe.

In some aspects, the measuring step comprises measuring the fluorescence of the probe at two or more time points selected from the group consisting of a first, second and third time point, wherein the temperature of the mixture is at or below the self-annealing temperature of the probe at the first time point, the temperature of the mixture is above the self-annealing temperature of the probe at the second time point, and the temperature of the mixture is at or below the self-annealing temperature of the probe at the third time point; and the method further comprises the step of raising the temperature of the mixture from a temperature at or below the self-annealing temperature of the probe to a temperature above the self-annealing temperature of the probe and the step of reducing the temperature of the mixture from a temperature above the self-annealing temperature of the probe to a temperature at or below the self-annealing temperature of the probe. For example, in some aspects, the determining step comprises comparing the fluorescence of the probe at the first and third time points with at least one threshold value. In some aspects, the determining step comprises comparing the fluorescence of the probe at the second and third time points with at least one threshold value. In some aspects, the determining step comprises comparing the difference of fluorescence of the probe at the first and second time points with the threshold value. In some aspects, the determining step comprises comparing the difference of fluorescence of the probe at the second and third time points with the threshold value.

In some aspects, the method comprises the step of raising the temperature of the mixture from a temperature at or below the self-annealing temperature of the probe to a temperature above the self-annealing temperature of the probe and the step of reducing the temperature of the mixture from a temperature above the self-annealing temperature of the probe to a temperature at or below the self-annealing temperature of the probe; and the measuring step comprises measuring the fluorescence of the probe after the reducing step at a temperature at or below the self-annealing temperature of the probe.

In some aspects, the method comprises the step of raising the temperature of the mixture from a temperature at or below the self-annealing temperature of the probe to a temperature above the self-annealing temperature of the probe; and the measuring step comprises measuring the fluorescence of the probe after the raising step at a temperature above the self-annealing temperature of the probe. In some aspects, the measuring step further comprises measuring the fluorescence of the probe at a temperature at or below the self-annealing temperature of the probe prior to the raising step.

In some aspects of the invention, the determining step comprises comparing the signal at two or more time points with two or more threshold values. In some aspects, the probe comprises an oligonucleotide labeled with a fluorophore and a quenching agent such that the probe is cleaved by 5' exonuclease activity of a DNA polymerase when the probe hybridizes to an amplified nucleic acid thereby emitting fluorescence.

In some aspects, the threshold value is based on the signal of an intact probe.

In some aspects, the probe is a molecular beacon.

In some aspects, at least part of the method is performed during an amplification reaction, the amplification reaction comprising (a) combining in an aqueous mixture:

(i) a target probe, a first control probe and a second control probe;

(ii) a first 5' primer, a first 3' primer and a target template, the target template comprising a hybridization site for the first 5' primer, the first 3' primer and the target probe;

(iii) a first control template, the first control template comprising a hybridization site for the first 5' primer, the first 3' primer and the first control probe; and (iv) a second 5' primer, a second 3' primer and a second control template, the second control template comprising a hybridization site for the second 5' primer, the second 3' primer, the target probe and a second control probe;

(b) performing an amplification reaction to create amplification products; and (c) quantifying binding of the target probe, first control probe and second control probe to the amplification products.

In some aspects, the method is practiced on at least two different probes in the mixture, wherein the probes are designed to hybridize to different nucleic acid sequences. In some aspects, the mixture further comprises a dye, and the method further comprises measuring a signal from the dye and normalizing the signal from the probe to the signal from the dye.

The present invention also provides apparatuses for testing the integrity of at least one probe for the detection of a nucleic acid, which probe is capable of binding a nucleic acid in a mixture. In some aspects, the apparatus comprises:

a) a temperature control system for changing the temperature of the mixture;

b) at least one detection mechanism for measuring a signal of the at least one probe; and c) a controller in communication with the temperature control system and the detection mechanism, wherein the controller is programmed to perform the steps of:

i) measuring the signal of the probe at one or more time point; and ii) determining the integrity of the probe by comparing the signal of the probe at the one or more time points with at least one threshold value.

In some aspects, the signal is fluorescence. In some aspects, the signal of the probe is measured when the probe is not bound to a target.

In some aspects, the probe comprises an oligonucleotide labeled with a fluorophore and a quenching agent such that the probe is cleaved by 5' exonuclease activity of a DNA polymerase when the probe hybridizes to an amplified nucleic acid thereby emitting fluorescence.

In some aspects, the probe comprises a fluorophore and a quenching agent, and heating the probe causes the probe to change conformation from a first conformation to a second conformation, thereby changing the distance between the fluorophore and the quenching agent such that the fluorescence of the fluorophore is quenched or altered in the first conformation compared to the fluorescence of the fluorophore in the second conformation.

In some aspects, the controller is programmed to:

measure the fluorescence of the probe at two or more time points selected from the group consisting of a first, second and third time point, wherein the temperature of the mixture is at or below the self-annealing temperature of the probe at the first time point, the temperature of the mixture is above the self-annealing temperature of the probe at the second time point, and the temperature of the mixture is at or below the self-annealing temperature of the probe at the third time point;

change the temperature of the mixture between the two or more time points; and compare the fluorescence of the probe at the two or more time points with at least one threshold value.

In some aspects, the signal of the probe is measured when the probe is not bound to a target. In some aspects, the controller is programmed to measure the fluorescence of the probe at a temperature at or below the self-annealing temperature of the probe. In some aspects, the controller is programmed to measure the fluorescence of the probe at a temperature above the self-annealing temperature of the probe.

In some aspects, the controller is programmed to raise the temperature of the mixture above the self-annealing temperature of the probe between the first and second time points and to reduce the temperature of the mixture to a temperature less than or equal to the self-annealing temperature of the probe between the second and third time points. In some aspects, the controller is programmed to compare the fluorescence of the probe at the first and third time points with at least one threshold value. In some aspects, the controller is programmed to compare the fluorescence of the probe at the second and third time points with at least one threshold value. In some aspects, the determining step comprises comparing the difference of fluorescence of the probe at the first and second time points with the threshold value. In some aspects, the determining step comprises comparing the difference of fluorescence of the probe at the second and third time points with the threshold value.

In some aspects, the controller is programmed to:

raise the temperature of the mixture from a temperature at or below the self-annealing temperature of the probe to a temperature above the self-annealing temperature of the probe;

reduce the temperature of the mixture from a temperature above the self-annealing temperature of the probe to a temperature at or below the self-annealing temperature of the probe; and measure the fluorescence of the probe after the reducing step at a temperature at or below the self-annealing temperature of the probe.

In some aspects, the controller is programmed to:

raise the temperature of the mixture from a temperature at or below the self-annealing temperature of the probe to a temperature above the self-annealing temperature of the probe; and measure the fluorescence of the probe at a temperature above the self-annealing temperature of the probe.

In some aspects, the controller is further programmed to measure the fluorescence of the probe at a temperature at or below the self-annealing temperature of the probe prior to the raising step. In some aspects, the threshold value is based on the signal of an intact control probe.

In some aspects, the controller is further programmed to measure the signal of at least two different probes in the mixture, and the probes are designed to hybridize to different nucleic acid sequences. In some aspects, the controller is programmed to measure a signal from a dye and to normalize the signal from the probe to the signal from the dye.

The present invention also provides computer program products readable by a machine. In some embodiments, the machine comprises at least one detection mechanism for measuring at one or more time points a signal of at least one probe for the detection of a nucleic acid sequence, and the machine comprises a temperature control system for changing the temperature of a mixture containing the probe, wherein the probe is capable of binding a nucleic acid.

In some aspects, the computer program products embody a program of instructions executable by the machine to perform the steps comprising:

(a) measuring a signal of the probe at one or more time points; and (b) determining the integrity of the probe by comparing the signal of the probe at the one or more time points with at least one threshold value.

In some aspects, the signal is fluorescence. In some aspects, the signal of the probe is measured when the probe is not bound to a target.

In some aspects, the probe comprises a fluorophore and a quenching agent, and heating the probe causes the probe to change conformation from a first conformation to a second conformation, thereby changing the distance between the fluorophore and the quenching agent such that the fluorescence of the fluorophore is quenched or altered in the first conformation compared to the fluorescence of the fluorophore in the second conformation.

In some aspects, the signal of the probe is measured when the probe is not bound to a target.

In some aspects, the measuring step comprises measuring the fluorescence of the probe at a temperature at or below the self-annealing temperature of the probe. In some aspects, the measuring step comprises measuring the fluorescence of the probe at a temperature above the self-annealing temperature of the probe.

In some aspects, the program of instructions further comprises steps of:

(a) measuring the fluorescence of the probe at two or more time points selected from the group consisting of a first, second and third time point, wherein the temperature of the mixture is at or below the self-annealing temperature of the probe at the first time point, the temperature of the mixture is above the self-annealing temperature of the probe at the second time point, and the temperature of the mixture is at or below the self-annealing temperature of the probe at the third time point; and (b) determining the integrity of the probe by comparing the fluorescence of the probe at the two or more time points with at least one threshold value.

In some aspects, the program of instructions further comprises the step of raising the temperature of the mixture above the self-annealing temperature of the probe and subsequently cooling the temperature of the mixture to a temperature less than or equal to the self-annealing temperature of the probe.

In some aspects, the determining step comprises comparing the fluorescence of the probe at the first and third time points with at least one threshold value. In some aspects, the determining step comprises comparing the fluorescence of the probe at the second and third time points with at least one threshold value. In some aspects, the determining step comprises comparing the difference of fluorescence of the probe at the first and second time points with the threshold value. In some aspects, the determining step comprises comparing the difference of fluorescence of the probe at the second and third time points with the threshold value.

In some aspects, the program of instructions further comprises steps of:

raising the temperature of the mixture from a temperature at or below the self-annealing temperature of the probe to a temperature above the self-annealing temperature of the probe;

reducing the temperature of the mixture from a temperature above the self-annealing temperature of the probe to a temperature at or below the self-annealing temperature of the probe; and measuring the fluorescence of the probe after the reducing step at a temperature at or below the self-annealing temperature of the probe.

In some aspects, the program of instructions further comprises the steps of:

raising the temperature of the mixture from a temperature at or below the self-annealing temperature of the probe to a temperature above the self-annealing temperature of the probe; and measuring the fluorescence of the probe at a temperature above the self-annealing temperature of the probe.

In some aspects, the program of instructions further comprises the step of measuring the fluorescence of the probe at a temperature at or below the self-annealing temperature of the probe prior to the raising step.

In some aspects, the threshold value is based on the signal of an intact probe. In some aspects, the program of instructions comprises determining the integrity of at least two different probes in the mixture, the probes being capable of binding to different nucleic acid sequences.

In some aspects, the program of instructions further comprises steps of:

measuring a signal from a dye and;

normalizing the signal from the probe to the signal from the dye.

The present invention also provides methods of detecting a target nucleic acid in a sample. In some aspects, the methods comprise, (a) providing a mixture comprising at least one probe capable of hybridizing with a target nucleic acid molecule, the probe comprising a fluorophore and a quenching agent, wherein heating the probe causes the probe to change conformation from a first conformation to a second conformation, thereby changing the distance between the fluorophore and the quenching agent such that the fluorescence of the fluorophore is quenched or altered in the first conformation compared to the fluorescence of the fluorophore in the second conformation;

(b) measuring a first fluorescence value of the probe at or below the self-annealing temperature of the probe;

(c) measuring a second fluorescence value of the probe above the self-annealing temperature of the probe;

(d) measuring a target fluorescence value of the probe when the probe is bound to the target nucleic acid; and (e) normalizing the target fluorescence value to the difference of the second fluorescence value and the first fluorescence value, whereby the normalized fluorescent value is indicative of the presence or amount of the target nucleic acid in the sample.

In some aspects, the target fluorescence is normalized by dividing the target fluorescence value by the difference of the second fluorescence value and the first fluorescence value. In some aspects, the probe is a molecular beacon.

In some aspects, the target nucleic acid is a product of an amplification reaction, the amplification reaction comprising:

(a) combining in an aqueous mixture:

(i) a target probe, a first control probe and a second control probe;

(ii) a first 5' primer, a first 3' primer and a target template, the target template comprising a hybridization site for the first 5' primer, the first 3' primer and the target probe;

(iii) a first control template, the first control template comprising a hybridization site for the first 5' primer, the first 3' primer and the first control probe; and (iv) a second 5' primer, a second 3' primer and a second control template, the second control template comprising a hybridization site for the second 5' primer, the second 3' primer, the target probe and a second control probe;

(b) performing an amplification reaction to create amplification products; and (c) quantifying binding of the target probe, first control probe and second control probe to the amplification products.

In some aspects, the methods further comprises quantifying an initial starting quantity or concentration of the target nucleic acid in the mixture using the normalized fluorescent value.

The present invention also provides apparatuses for normalizing the fluorescence of at least one probe to quantify a polynucleotide in a mixture, the probe being capable of hybridizing with a target nucleic acid molecule and the probe comprising a fluorophore and a quenching agent, wherein heating the probe causes the probe to change conformation from a first conformation to a second conformation, thereby changing the distance between the fluorophore and the quenching agent such that the fluorescence of the fluorophore is quenched or altered in the first conformation compared to the fluorescence of the fluorophore in the second conformation. In some aspects, the apparatus comprises:

a) at least one detection mechanism for measuring the fluorescence of the probe; and b) a controller in communication with the detection system, wherein the controller is programmed to perform the steps comprising:

(i) measuring:

1) a first fluorescence value of the probe at or below the self-annealing temperature of the probe;

2) a second fluorescence value of the probe above the self-annealing temperature of the probe; and 3) a target fluorescence value of the probe when the probe is bound to a target nucleic acid; and (ii) normalizing the target fluorescence value to the difference of the second fluorescence value and the first fluorescence value.

In some aspects, the controller is programmed to quantify an initial starting quantity or concentration of the target nucleic acid in the mixture using the normalized fluorescent value. In some aspects, the target fluorescence is normalized by dividing the target fluorescence value by the difference of the second fluorescence value and the first fluorescence value. In some aspects, the apparatus further comprises a temperature control system for raising the temperature of the mixture above a self-annealing temperature of the probe and for cooling the temperature of the mixture to a temperature less than or equal to the self-annealing temperature of the probe.

The present invention also provides computer program products readable by a machine having at least one detection mechanism for measuring the fluorescence of at least one probe in a mixture, the probe being capable of hybridizing with a target nucleic acid molecule, and the probe comprising a fluorophore and a quenching agent, wherein heating the probe causes the probe to change conformation from a first conformation to a second conformation, thereby changing the distance between the fluorophore and the quenching agent such that the fluorescence of the fluorophore is quenched or altered in the first conformation compared to the fluorescence of the fluorophore in the second conformation. In some aspects, the computer program products embody a program of instructions executable by the machine to perform the steps comprising:

(a) measuring a first fluorescence value of the probe at or below the self-annealing temperature of the probe;

(b) measuring a second fluorescence value of the probe above the self-annealing temperature of the probe;

(c) measuring a target fluorescence value of the probe when the probe is bound to a target nucleic acid; and (d) normalizing the target fluorescence value to the difference of the second fluorescence value and the first fluorescence value.

In some aspects, the program of instructions further comprises the step of normalizing the target fluorescence value by dividing the target fluorescence value by the difference of the second fluorescence value and the first fluorescence value. In some aspects, the program of instructions further comprises the step of quantifying an initial starting quantity or concentration of the target nucleic acid in the mixture using the normalized fluorescent value. In some aspects, the program of instructions further comprises the step of comparing the target fluorescence value of at least two different probes, each probe designed to hybridize to a different target polynucleotides in one sample.

In some aspects, the machine further comprises a temperature control system for raising the temperature of a mixture containing the probe above a self-annealing temperature of the probe and for cooling the temperature of the mixture to a temperature less than or equal to the self-annealing temperature of the probe, and the program of instructions further comprises the steps of raising the temperature of a mixture containing the probe above a self-annealing temperature of the probe and for cooling the temperature of the mixture to a temperature less than or equal to the self-annealing temperature of the probe.

The present invention also provides methods of detecting a target nucleic acid in a sample. For example, in some aspects, the methods comprise:

(a) providing a mixture comprising at least one probe which is capable of binding to a nucleic acid;

(b) measuring a test signal value of the probe;

(c) measuring a target signal value of the probe when the probe is bound to a target nucleic acid; and (d) normalizing the target signal value to the test signal value of the probe, whereby the normalized signal value is indicative of the presence or amount of the target nucleic acid in the sample.

In some aspects, the target signal value is normalized by dividing the target signal value by the test signal value of the probe. In some aspects, the signal is fluorescence. In some aspects, the test signal value is measured when the probe is not bound to the target nucleic acid.

In some aspects, the test signal value is measured when the mixture is at a temperature above the self-annealing temperature of the probe. In some aspects, the test signal value is measured when the probe is not bound to the target nucleic acid and the mixture is at a temperature above the self-annealing temperature of the probe. In some aspects, the test signal value is measured when the mixture is at a temperature below or equal to the self-annealing temperature of the probe. In some aspects, the probe is capable of hybridizing with a target nucleic acid molecule, the probe comprising a fluorophore and a quenching agent, wherein heating the probe causes the probe to change conformation from a first conformation to a second conformation, thereby changing the distance between the fluorophore and the quenching agent such that the fluorescence of the fluorophore is quenched or altered in the first conformation compared to the fluorescence of the fluorophore in the second conformation.

In some aspects, the probe comprises an oligonucleotide labeled with a fluorophore and a quenching agent such that the probe is cleaved by 5' exonuclease activity of a DNA polymerase when the probe hybridizes to an amplified nucleic acid, thereby emitting fluorescence. In some aspects, methods further comprise comparing the normalized target fluorescence value of at least two different probes, wherein each probe is designed to hybridize to a different target polynucleotides in one sample.

In some aspects, the probe is a molecular beacon.

In some aspects, the target polynucleotide is a product of an amplification reaction, the amplification reaction comprising (a) combining in an aqueous mixture:

(i) a target probe, a first control probe and a second control probe;

(ii) a first 5' primer, a first 3' primer and a target template, the target template comprising a hybridization site for the first 5' primer, the first 3' primer and the target probe;

(iii) a first control template, the first control template comprising a hybridization site for the first 5' primer, the first 3' primer and the first control probe; and (iv) a second 5' primer, a second 3' primer and a second control template, the second control template comprising a hybridization site for the second 5' primer, the second 3' primer, the target probe and a second control probe;

(b) performing an amplification reaction to create amplification products; and (c) quantifying binding of the target probe, first control probe and second control probe to the amplification products.

In some aspects, the methods further comprise quantifying an initial starting quantity or concentration of the target nucleic acid in the mixture using the normalized fluorescent value.

The present invention also provides apparatuses for normalizing the signal of at least one probe, wherein the probe is capable of binding a nucleic acid in a mixture. In some aspects, the apparatus comprises;

a) at least one detection mechanism for measuring a signal of the probe; and b) a controller in communication with the detection mechanism, wherein the controller is programmed to perform the steps comprising:

(i) measuring a test signal value of the probe;

(ii) measuring a target signal value of the probe when the probe is bound to a target nucleic acid; and (iii) normalizing the target signal value to the test signal value of the probe.

In some aspects, the target signal value is normalized by dividing the target fluorescence value by the test signal value of the probe. In some aspects, the controller is further programmed to quantify an initial starting quantity or concentration of the target nucleic acid in the mixture using the normalized fluorescent value. In some aspects, the signal is fluorescence.

In some aspects, the probe is capable of hybridizing with a target nucleic acid molecule and the probe comprises a fluorophore and a quenching agent, wherein heating the probe causes the probe to change conformation from a first conformation to a second conformation, thereby changing the distance between the fluorophore and the quenching agent such that the fluorescence of the fluorophore is quenched or altered in the first conformation compared to the fluorescence of the fluorophore in the second conformation; and the apparatus comprises a temperature control system for raising the temperature of the mixture above a self-annealing temperature of the probe and for cooling the temperature of the mixture to a temperature less than or equal to the self-annealing temperature of the probe.

In some aspects, the test signal value is measured when the probe is not bound to the target nucleic acid. In some aspects, the test signal value is measured when the mixture is at a temperature above the self-annealing temperature of the probe. In some aspects, the test signal value is measured when the mixture is at a temperature below or equal to the self-annealing temperature of the probe. In some aspects, the test signal value is measured when the probe is not bound to the target nucleic acid and the mixture is at a temperature above the self-annealing temperature of the probe. In some aspects, the controller is further programmed to compare the normalized target signal value of at least two different probes, each probe designed to hybridize to a different target polynucleotide in one sample.

The present invention also provides computer program products readable by a machine having at least one detection mechanism for measuring the signal of at least one probe in a mixture, wherein the probe is capable of binding to a nucleic acid. For example, in some aspects, the computer program products embody a program of instructions executable by the machine to perform the steps comprising:

(a) measuring a test signal value of the probe;

(b) measuring a target signal value of the probe when the probe is bound to a target nucleic acid; and (c) normalizing the target signal value to the test signal value of the probe.

In some aspects, the program of instructions further comprises the step of normalizing the target signal value by dividing the target signal value by the test signal value of the probe. In some aspects, the program of instructions further comprises the step of quantifying an initial starting quantity or concentration of the target nucleic acid in the mixture using the normalized fluorescent value. In some aspects, the signal is fluorescence. In some aspects, the program of instructions further comprises the step of comparing the normalized target signal value of at least two different probes, wherein each probe is designed to hybridize to different target polynucleotides in one sample.

In some aspects, the probe is capable of hybridizing with a target nucleic acid molecule, and the probe comprises a fluorophore and a quenching agent, wherein heating the probe causes the probe to change conformation from a first conformation to a second conformation, thereby changing the distance between the fluorophore and the quenching agent such that the fluorescence of the fluorophore is quenched or altered in the first conformation compared to the fluorescence of the fluorophore in the second conformation; and wherein the machine further comprises a temperature control system for raising the temperature of a mixture containing the probe above a self-annealing temperature of the probe and for cooling the temperature of the mixture to a temperature less than or equal to the self-annealing temperature of the probe, and wherein the program of instructions further comprises the steps of raising the temperature of a mixture containing the probe above a self-annealing temperature of the probe and for cooling the temperature of the mixture to a temperature less than or equal to the self-annealing temperature of the probe.

In some aspects, the test signal value is measured when the probe is not bound to the target nucleic acid. In some aspects, the test signal value is measured when the mixture is at a temperature above the self-annealing temperature of the probe. In some aspects, the test signal value is measured when the mixture is at a temperature below or equal to the self-annealing temperature of the probe. In some aspects, the test signal value is measured when the probe is not bound to the target nucleic acid and the mixture is at a temperature above the self-annealing temperature of the probe.

DEFINITIONS

An "amplification reaction" refers to any chemical, including enzymatic, reaction that results in increased copies of a template nucleic acid sequence. Amplification reactions include polymerase chain reaction (PCR) and ligase chain reaction (LCR) (see U.S. Pat. Nos. 4,683,195 and 4,683,202; *PCR Protocols: A Guide to Methods and Applications* (Innis et al., eds, 1990)), strand displacement amplification (SDA) (Walker, et al. *Nucleic Acids Res.* 20(7):1691–6 (1992); Walker *PCR Methods Appl* 3(1):1–6 (1993)), transcription-mediated amplification (Phyffer, et al., *J. Clin. Microbiol.* 34:834–841 (1996); Vuorinen, et al., *J. Clin. Microbiol.* 33:1856–1859 (1995)), nucleic acid sequence-based amplification (NASBA) (Compton, *Nature* 350(6313):91–2 (1991), rolling circle amplification (RCA) (Lisby, *Mol. Biotechnol.* 12(1):75–99 (1999)); Hatch et al., *Genet. Anal.* 15(2):35–40 (1999)) and branched DNA signal amplification (bDNA) (see, e.g., Iqbal et al, *Mol. Cell Probes* 13(4):315–320 (1999)).

A "computer program product" refers to a program of instructions executable by a machine such as a computer or processor to perform a specified series of steps. The computer program product (e.g., software) readable by a controller may comprise a storage medium (e.g., a disk) embodying the program instructions. Alternatively, the computer program product may be an electronic file stored in the memory of the controller or downloadable to the controller.

A "controller" refers to a computer (e.g., a personal or network computer), processor or microprocessor.

A "detection mechanism" refers to a mechanism for measuring at least one signal whose intensity is related to the quantity or concentration of a nucleic acid sequence in a mixture. Preferred detection mechanisms measure signals detectable by fluorescence, radioactivity, colorimetry, X-ray diffraction or absorption, magnetism, or enzymatic activity. Another suitable detection mechanism for use in the present invention detects and measures one or more electrical signals (e.g., measurements of electrical conductance, inductance, resistance, or capacitance) indicative of the quantity or concentration of a nucleic acid sequence.

The term "fluorophore" refers to chemical compounds which, when excited by exposure to particular wavelengths of light, emit light (i.e. fluoresce) at a different wavelength. When the excited-state energy of the fluorophore is transferred to a non-fluorophore acceptor, the fluorescence of the fluorophore is quenched without subsequent emission of fluorescence by the acceptor. In this case, the acceptor functions as a "quenching agent."

The phrase "integrity of a probe" refers to how intact a probe is. If the integrity of the probe is disrupted, then the probe does not function as well, for example, because its ability to emit a signal in the presence of a target nucleic acid is disrupted. The integrity can be disrupted, for instance, by cleavage of the body of the probe or by cleavage of the signal generating agent, e.g., a fluorophore or quenching agent.

The phrase "molecular beacon" refers to a probe described in, e.g., Tyagi and Kramer (*Nature Biotech.* 14:303–309 (1996)) and U.S. Pat. Nos. 5,119,801 and 5,312,728. For instance, molecular beacons typically comprise a fluorophore and a quenching agent. Heating the probe causes the probe to change conformation from a first conformation to a second conformation, thereby changing the distance between the fluorophore and the quenching agent such that the fluorescence of the fluorophore is quenched or altered in the first conformation compared to the fluorescence of the fluorophore in the second conformation.

"Normalizing" refers to a process for rescaling a quantity. For example, the signal output of a probe is normalized to reduce variations between readings in a mixture or between mixtures. Signals are typically normalized to a particular reference value or a reference reading.

The phrase "nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

A "probe" refers to a composition comprising a polynucleotide sequence capable of hybridization to and detection of a nucleic acid sequence of interest. Such probes are useful in, e.g., hybridization assays, including fluorescence in situ hybridizations (FISH) (see, e.g., Sokol, et al. *Proc. Natl. Acad Sci. USA* 95:11538–11543 (1998) and Matsuo, *Biochimica Biophysica Acta* 1379:178–184 (1998)) as well as in amplification reactions. For example, "probes" can comprise polynucleotides linked to fluorescent or radioactive reagents, thereby allowing for the detection of these reagents. Examples of probes of the invention include, e.g., molecular beacons (See, e.g., U.S. Pat. No. 5,925,517 and Tyagi, S. and Kramer, F. R., *Nature Biotechnology* 14: 303–308 (1996)), "scorpion probes" (see, e.g., Whitcombe, et al., *Nature Biotechnology* 17:804–807 (1999)) and Taqman® probes (see, e.g., Livak, K. J., et al., *PCR Methods Appl.* 4(6): 357–362 (1995)), peptide nucleic acid probes (PNAs) (see, e.g., Ortiz, E., G. Estrada and P. M. Lizardi, *Molecular and Cellular Probes* 12, 219–226 (1998)) as well as other probes that utilize FRET technology. An "intact probe" refers to a probe that is not cleaved or degraded.

A "self-annealing temperature" of a probe refers to the temperature at or below which a probe forms a secondary structure sufficient to quench the fluorescence of the probe relative to the fluorescence of the probe when the secondary structure is not formed. A self-annealing temperature of a probe is generally used in reference to probes comprising a fluorophore and a quenching agent, wherein heating the probe causes the probe to change conformation from a first conformation to a second conformation, thereby changing the distance between the fluorophore and the quenching agent such that the fluorescence of the fluorophore is quenched or altered in the first conformation compared to the fluorescence of the fluorophore in the second conformation. Examples of probes that can self-anneal include molecular beacons and scorpion probes.

A "target" or "target nucleic acid" refers to a single or double stranded polynucleotide sequence sought to be amplified in an amplification reaction.

A "target fluorescence value" or "target signal value" refers to the signal produced by a probe when it is bound to a target sequence.

A "template" refers to a single-stranded or double-stranded polynucleotide sequence that comprises the polynucleotide to be amplified.

A "test signal value" refers to the signal emitted from a probe when the probe is not bound or hybridized to its target nucleic acid. For example, a molecular probe would typically be tested at a temperature above the temperature where it would hybridize to its target. A Taqman® probe can be tested in the presence of a target sequence, so long as the Taqman® probe is not activated by the 5' exonuclease activity of a polymerase.

DESCRIPTION OF THE SPECIFIC EMBODIMENTS

I. Introduction

Figure 1:
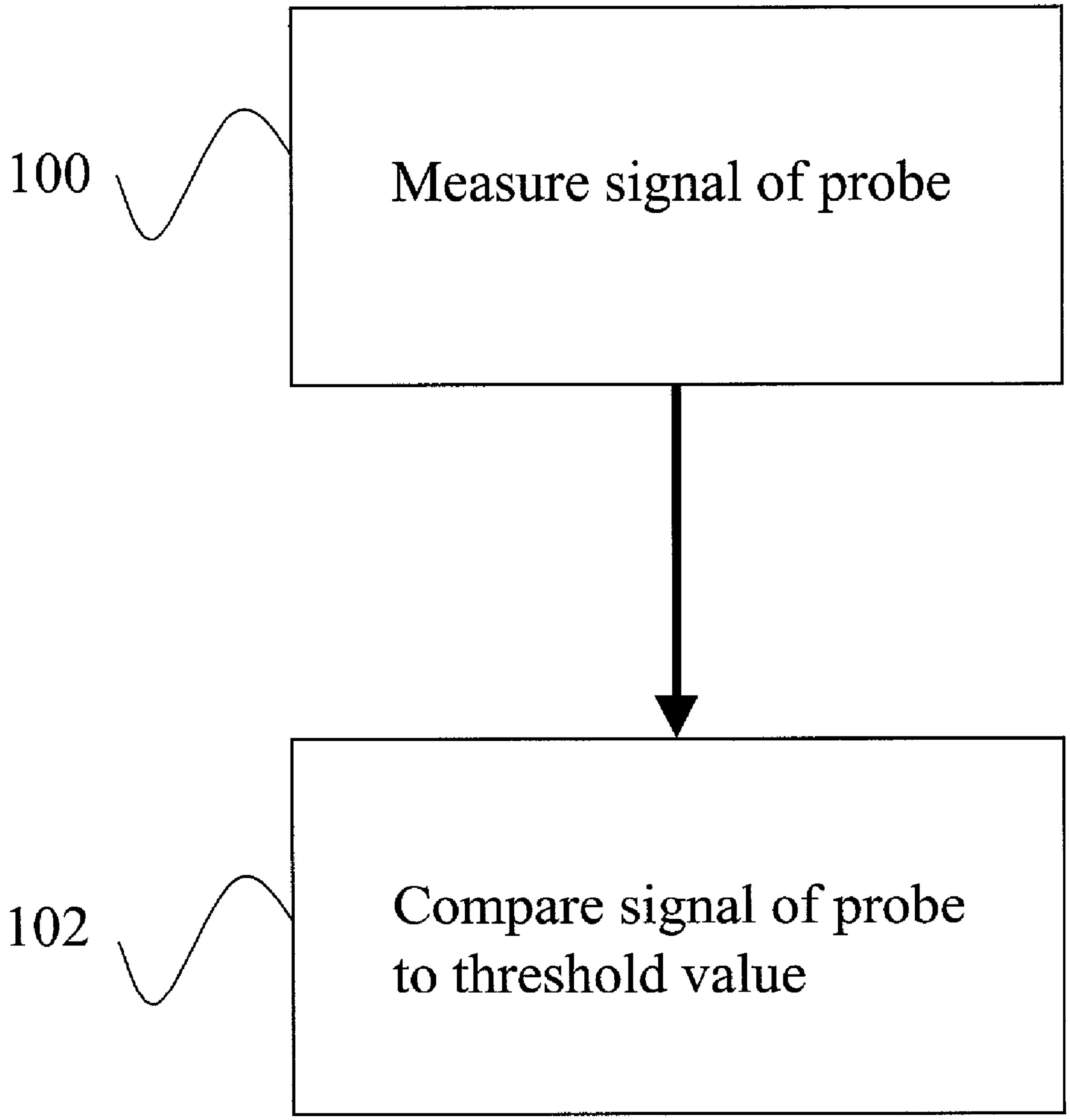
FIG. 1 is a flowchart illustrating a general method of determining the integrity of a probe.

The present invention provides methods, apparatuses and computer programs for verifying the integrity of a probe by comparing the signal of a probe to a threshold value. The methods of the invention, referred to herein generally as the "probe check assay", thereby remove the necessity to use an external positive control to confirm the integrity of the probe. The methods of the invention involve comparing the fluorescence of a fluorescent probe at one or more temperatures to the fluorescence of an intact probe or to a predetermined value or range. For example, FIG. 1 is a flowchart illustrating a general probe check method of the invention. Variation of the probe fluorescence from the comparative value indicates that the probe may have failed. Of course, those of skill in the art will recognize that the probe check assay is useful to detect the integrity of each probe in a mixture if more than one probe is in a mixture.

II. Probes That Change Conformation in Response to Temperature Changes

Many types of molecular probes produce signals, typically in the form of fluorescence, when the probe binds its nucleic acid target, but do not produce signal when unbound. These probes rely on the formation of a hairpin loop, or some other structure when the probe is not binding the target, to bring a fluorophore and a quenching agent within proximity to each other, thereby quenching the signal from the fluorophore.

For probes that have altered fluorescence at different temperatures, such as molecular beacons, fluorescence at one or more temperatures can be used to determine the integrity of the probe. Such probes can be placed in a reaction mixture and then the temperature of the reaction mixture can be modulated. By comparing the signal produced by the probe at at least one temperature to a threshold value, the integrity of the probe can be determined. For example, the signal produced by the probe can be measured at one or more of the following time points and temperatures: a first time point when the mixture containing the probe is at a temperature T1 equal to or below the self-annealing temperature of the probe; a second time point when the mixture has been raised to a temperature T2 above the self-annealing temperature of the probe; or a third time point when the mixture has been cooled to a temperature T3 equal to or below the self-annealing temperature of the probe. As used throughout this document, temperature T1 represents a temperature at or below the self-annealing temperature of the probe, temperature T2 represents a temperature above the self-annealing temperature of the probe, and temperature T3 represents a temperature equal to or below the self-annealing temperature of the probe. Temperature T3 may be equal to temperature T1 or temperature T3 may differ from temperature T1 as long as both temperatures T1 and T3 are equal to or below the self-annealing temperature of the probe.

Figure 7:
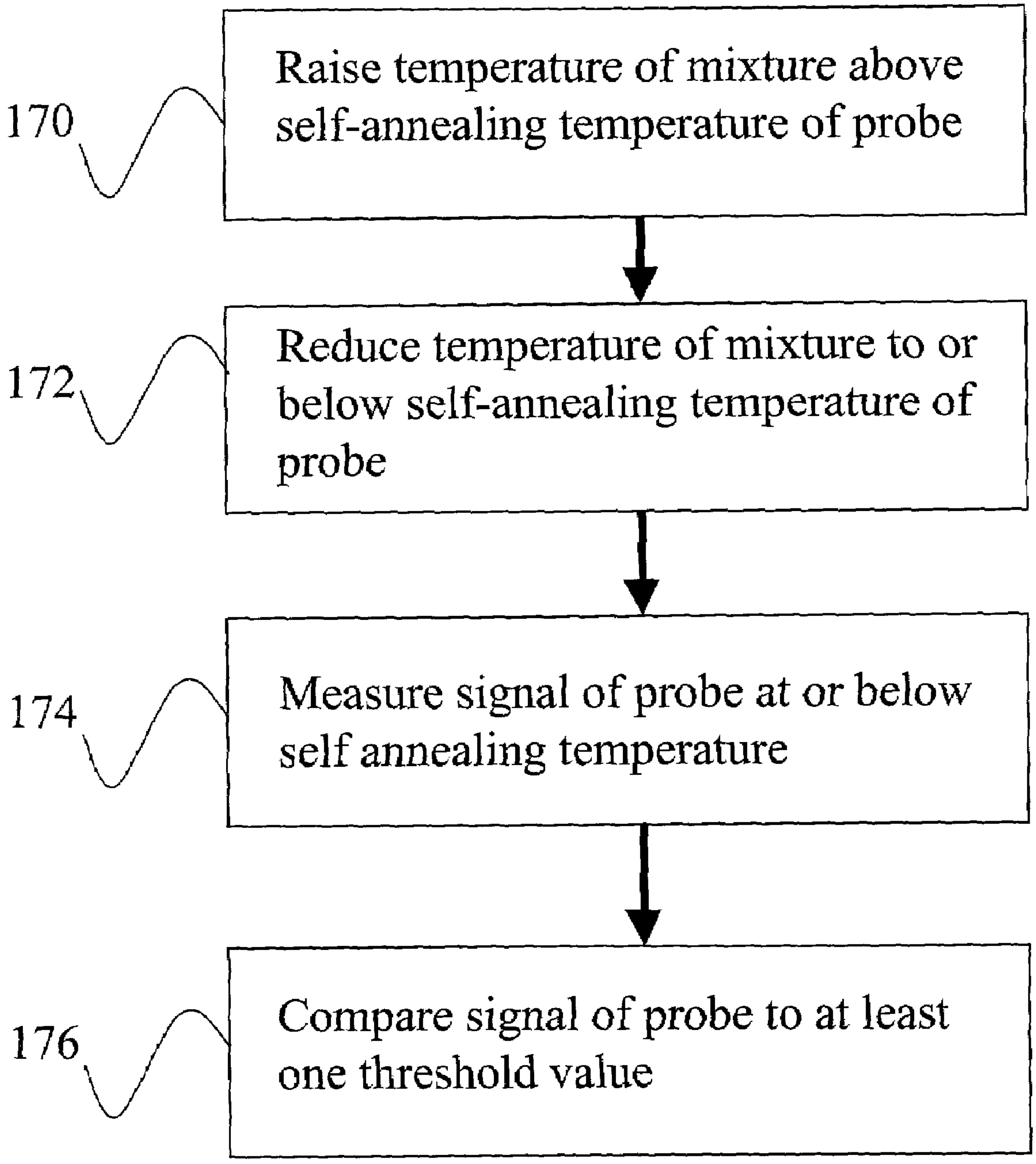
FIG. 7 is a flowchart illustrating some embodiments of the methods of determining the integrity of a probe.

Prior to beginning a hybridization (e.g., before beginning the amplification of target), the signal (e.g., fluorescence) of a probe in the reaction mixture is read at at least one of the following time points: a first time point when the mixture is at temperature T1; a second time point when the mixture has been raised to temperature T2; or a third time point when the mixture has been cooled to temperature T3. Probe signal readings at temperature T1, temperature T2, or temperature T3 that are outside the predetermined limits for an intact fully functional probe suggest that the integrity of the probe is different from an intact fully functional probe and indicate that a PCR assay, or other amplification reactions monitored by that probe, would fail. For instance, FIG. 7 is a flowchart illustrating a step 170 of raising the temperature of a mixture containing a probe above the self-annealing temperature of the probe, a step 172 of reducing the temperature of the mixture to or below the self-annealing temperature of the probe, a step 174 of measuring the signal of the probe at or below the self-annealing temperature and a step 176 of comparing the signal of the probe to at least one threshold value.

In some embodiments, the initial signal of a probe is determined and compared with the signal from an intact probe or a predetermined value or range with a known relationship to an intact probe. Variation of the initial fluorescence from the signal from an intact probe or a predetermined value indicates degradation of the probe. Predetermined threshold values, which might include upper and lower acceptance limits, can be specific to a lot of reagent or applicable to all lots of reagents.

Figure 3:
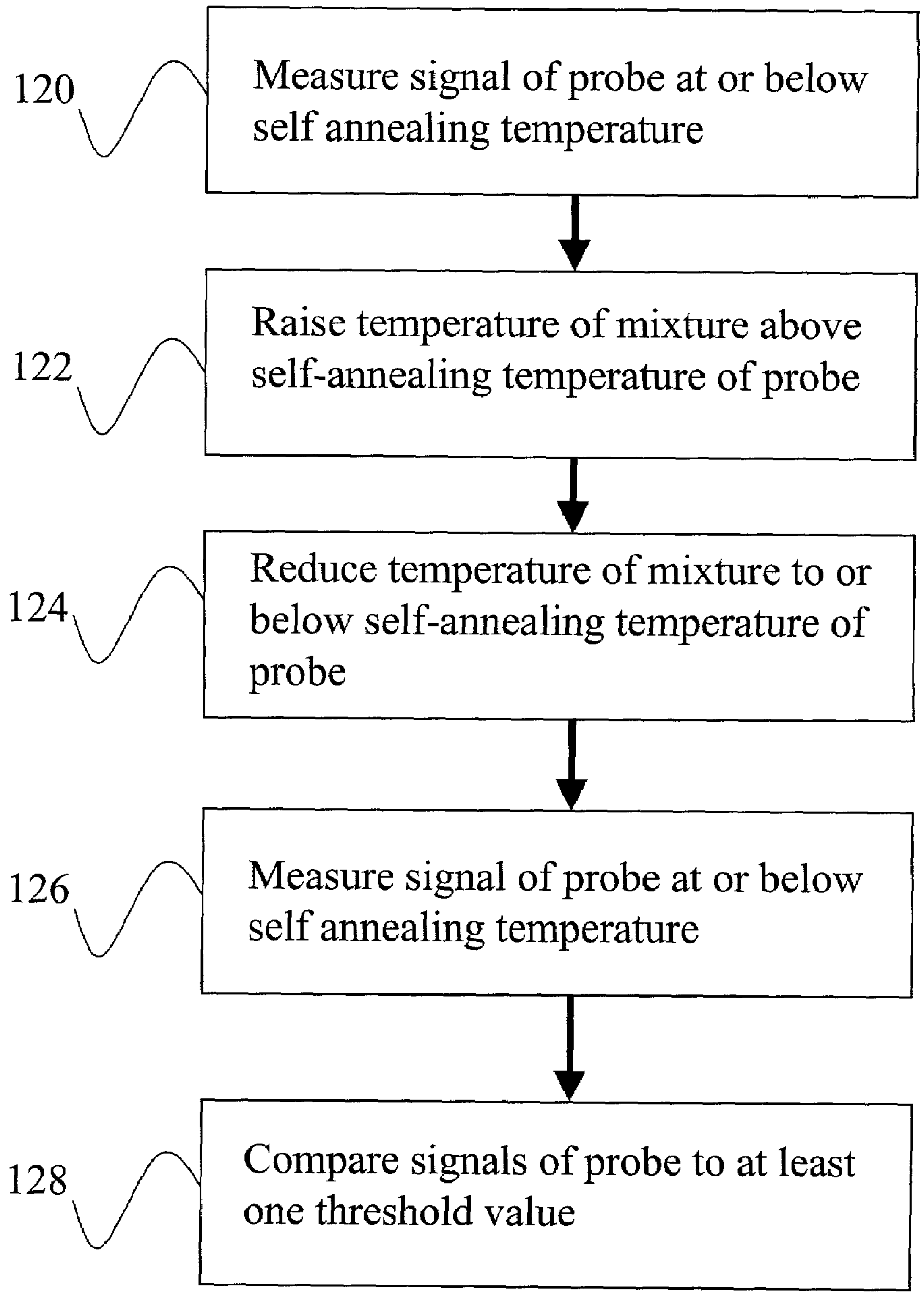
FIG. 3 is a flowchart illustrating some embodiments of the methods of determining the integrity of a probe.

In some embodiments, the signal of the probe is measured at more than one time point to determine the integrity of the probe. For example, FIG. 3 shows an embodiment in which the probe signal is measured at two time points. In step 120, the signal of the probe is measured at temperature T1 below the self-annealing temperature of the probe. In step 122, the temperature of the mixture containing the probe is raised to temperature T2 above the self-annealing temperature of the probe. In step 124, the temperature of the mixture is reduced to temperature T3 that is equal to or below the self-annealing temperature of the probe. In step 126, the probe signal is measured at temperature T3. In step 128, the signals measured at the different time points are compared to at least one threshold value to determine the integrity of the probe. For example, each measured signal may be compared to a single threshold value or compared to upper and lower threshold values defining an acceptable range for the signal.

Figure 5:
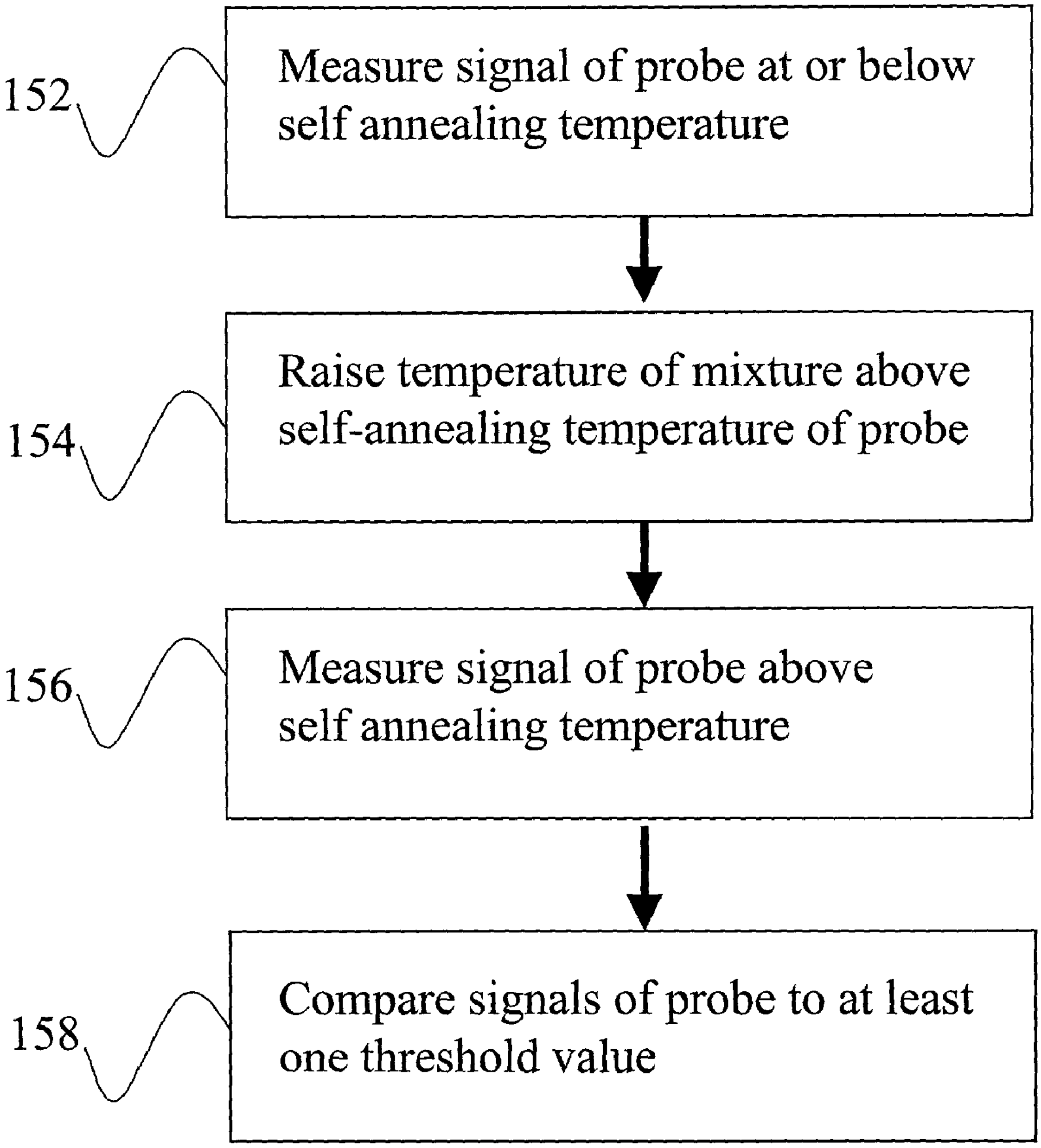
FIG. 5 is a flowchart illustrating some embodiments of the methods of determining the integrity of a probe.

FIG. 5 shows an embodiment of the invention in which the probe signal is measured at two different temperatures to determine the integrity of the probe. In step 152, the signal of the probe is measured at temperature T1 equal to or below the self-annealing temperature of the probe. In step 154, the temperature of the mixture containing the probe is raised to temperature T2 above the self-annealing temperature of the probe. In step 156, the probe signal is measured at temperature T2. In step 158, the signals measured at the different temperatures are compared to at least one threshold value to determine the integrity of the probe. For example, the signal measured at temperature T1 may be compared to a first threshold value and the signal measured at temperature T2 compared to a second threshold value. Alternatively, the signal measured at temperature T1 may be compared to first and second threshold values defining an acceptable range for the signal, and the signal measured at temperature T2 may be compared to third and fourth threshold values defining an acceptable range for the signal.

Figure 6:
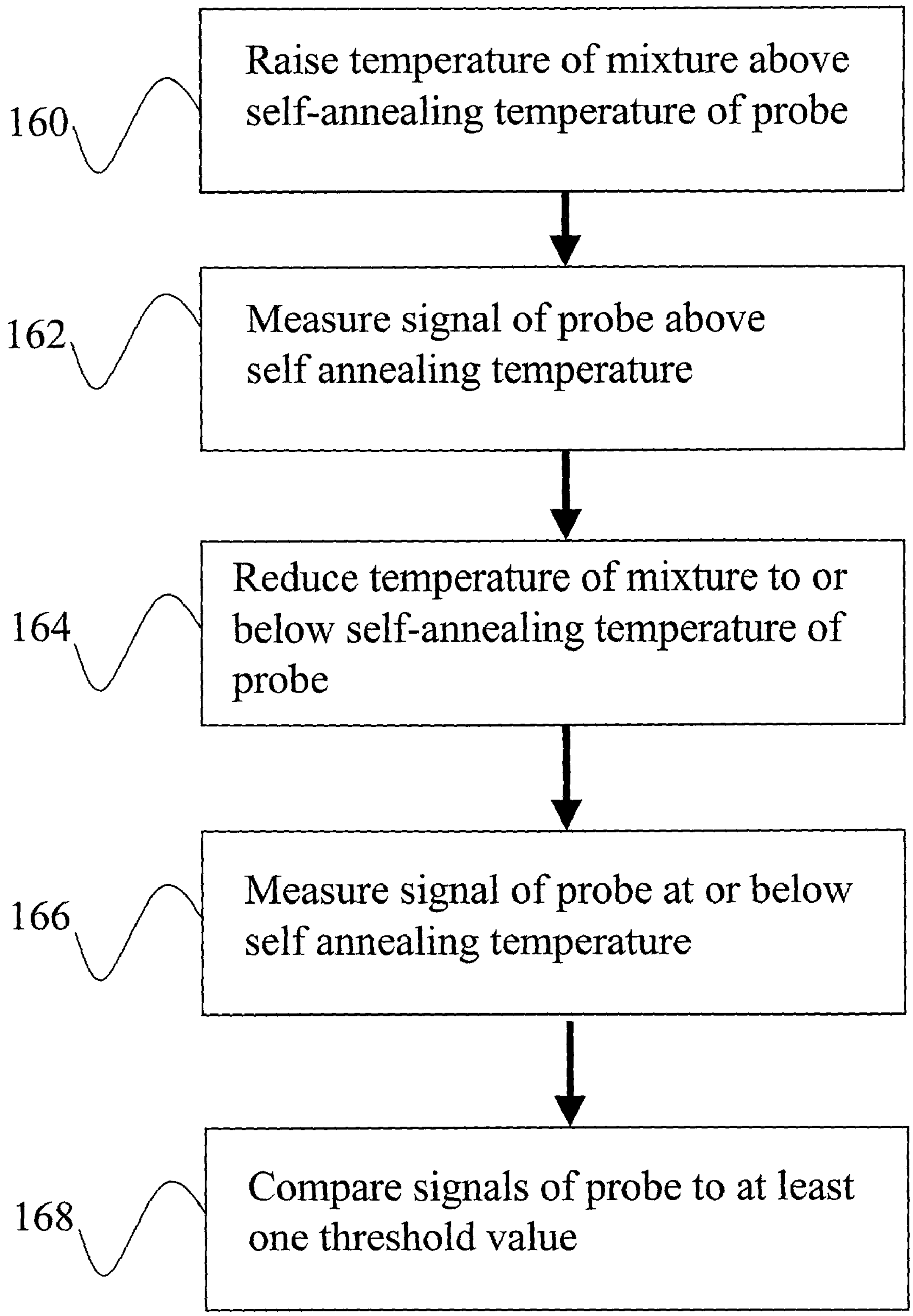
FIG. 6 is a flowchart illustrating some embodiments of the methods of determining the integrity of a probe.

FIG. 6 shows another embodiment of the invention in which the probe signal is measured at two different temperatures to determine the integrity of the probe. In step 160, the temperature of the mixture containing the probe is raised to temperature T2 above the self-annealing temperature of the probe. In step 162, the probe signal is measured at temperature T2. In step 164, the temperature of the mixture is reduced to temperature T3 that is equal to or below the self-annealing temperature of the probe. In step 166, the signal of the probe is measured at temperature T3. In step 168, the signals measured at the different temperatures are compared to at least one threshold value to determine the integrity of the probe. For example, the signal measured at temperature T2 may be compared to a first threshold value and the signal measured at temperature T3 compared to a second threshold value. Alternatively, the signal measured at temperature T2 may be compared to first and second threshold values defining an acceptable range for the signal, and the signal measured at temperature T3 may be compared to third and fourth threshold values defining an acceptable range for the signal.

Figure 2:
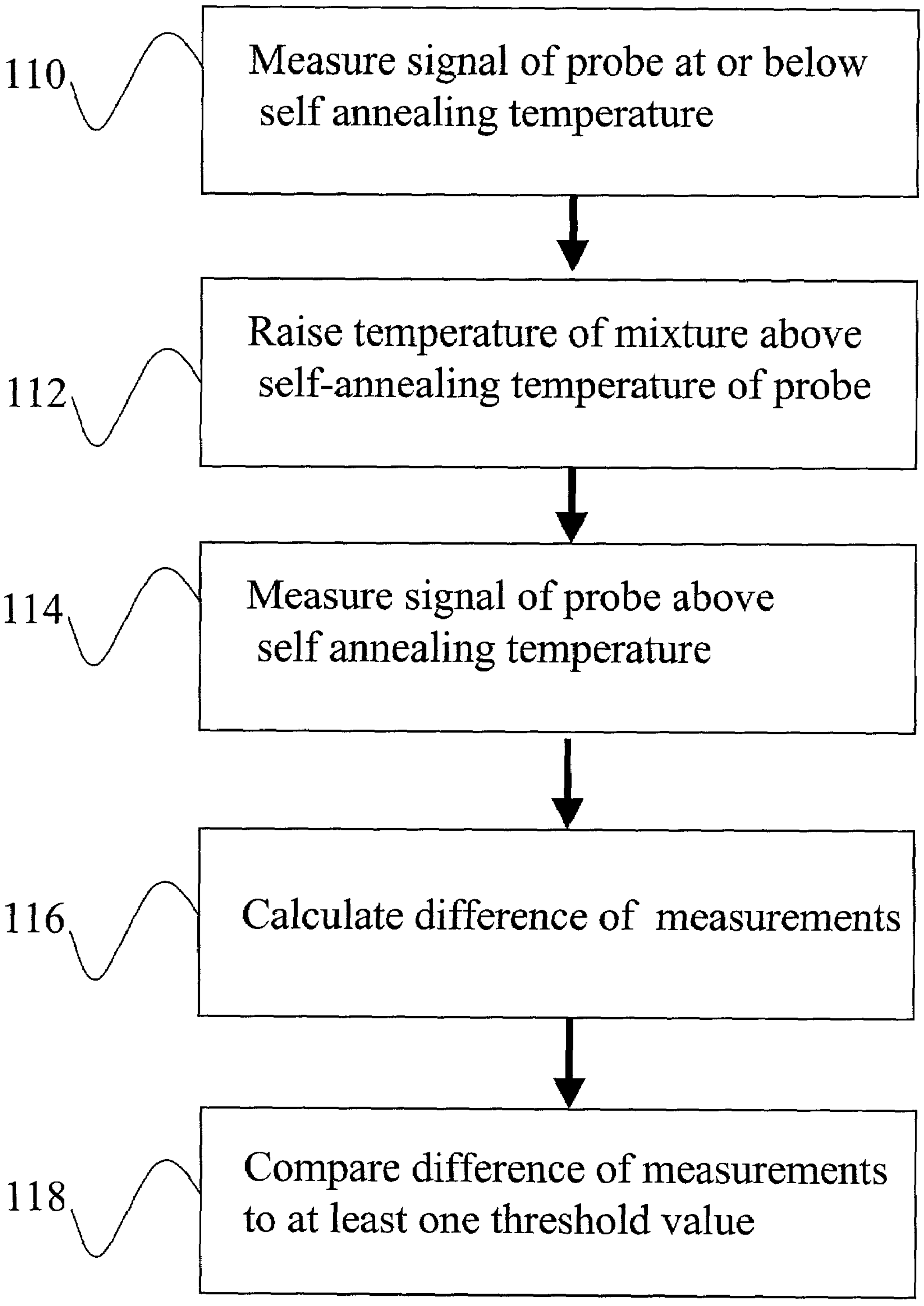
FIG. 2 is a flowchart illustrating some embodiments of the methods of determining the integrity of a probe.

In other embodiments, the difference of signals measured at different time points or temperatures is calculated and compared to at least one threshold value. For example, FIG. 2 shows an embodiment in which the difference of probe signals measured at temperatures T1 and T2 is used to determine the integrity of the probe. In step 110, the signal of the probe is measured at temperature T1 at or below the self-annealing temperature of the probe. In step 112, the temperature of the mixture containing the probe is raised to temperature T2 above the self-annealing temperature of the probe. In step 114, the signal of the probe is measured at temperature T2. In step 116, the difference of the two measurements is calculated. In step 118, the difference of the measurements is compared to at least one threshold value. For example, the difference in measurements may be compared to a single threshold value or compared to upper and lower threshold values defining an acceptable range for the difference in measurements.

Figure 4:
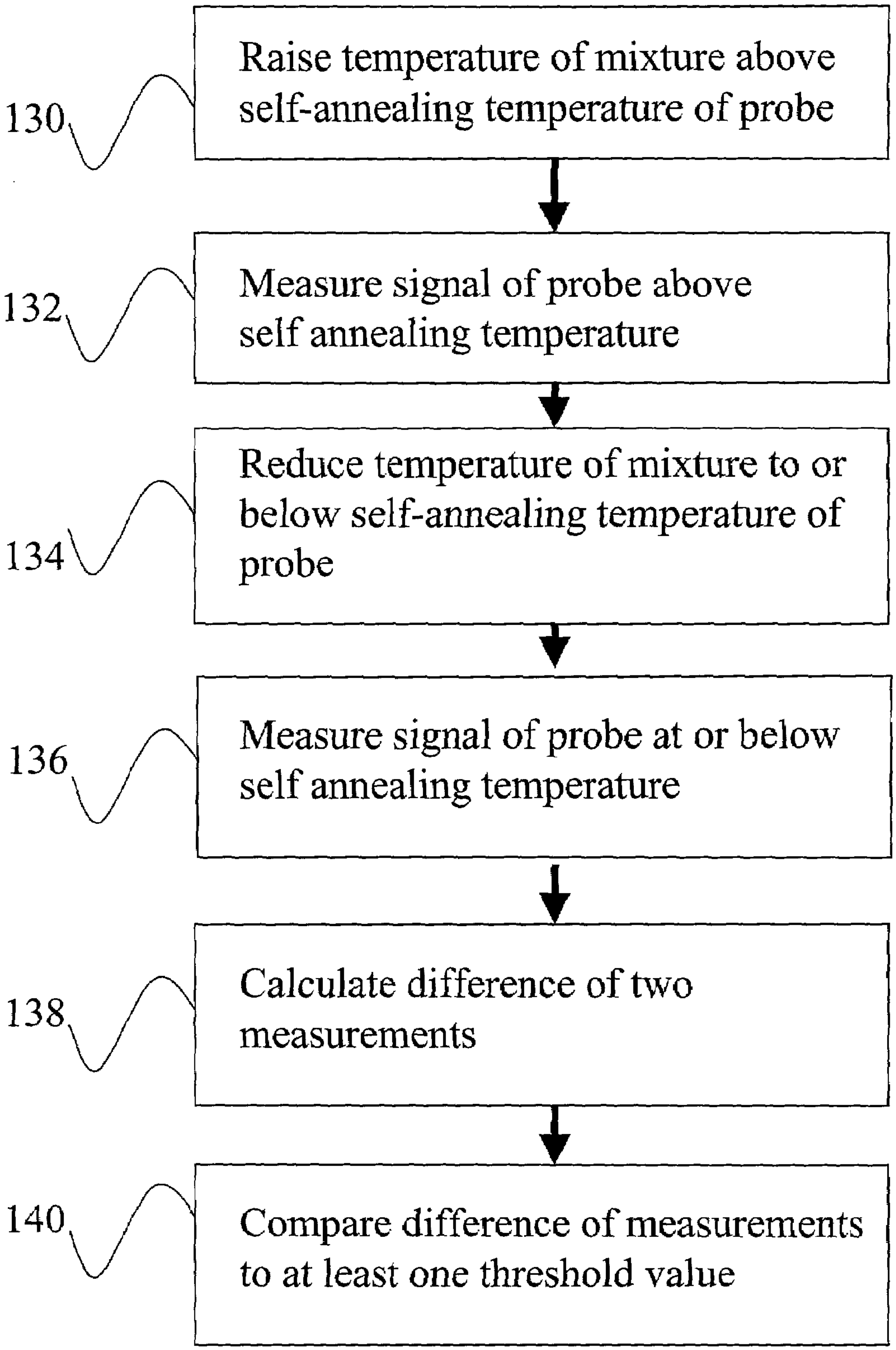
FIG. 4 is a flowchart illustrating some embodiments of the methods of determining the integrity of a probe.

FIG. 4 shows another embodiment of the invention in which the difference of signals measured at different temperatures is calculated and compared to at least one threshold value. In step 130, the temperature of the mixture containing the probe is raised to temperature T2 above the self-annealing temperature of the probe. In step 132, the signal of the probe is measured at temperature T2. In step 134, the temperature of the mixture is reduced to temperature T3 that is equal to or below the self-annealing temperature of the probe. In step 136, the signal of the probe is measured at temperature T3. In step 138, the difference of the two measurements taken at temperatures T2 and T3 is calculated. In step 140, the difference of the measurements is compared to at least one threshold value. For example, the difference in measurements may be compared to a single threshold value or compared to upper and lower threshold values defining an acceptable range for the difference in measurements.

A summary of some possible scenarios of probe failure is provided below. For example, if the probe structure is cleaved, then the probe will not properly self-anneal at temperature T3, and therefore will produce a different, and typically higher, signal than the signal measured at temperature T1. In a different embodiment, the quenching agent of the probe is cleaved. In that situation, the signal measured at both temperature T1 and temperature T3 will be high compared to the threshold value (i.e., based on an intact probe signal). In addition, the difference in signals between temperatures T1 and T2 or the difference in signals between temperatures T3 and T2 will not significantly differ because the quenching agent will not quench the fluorophore at any temperature.

A list of some possible probe modifications and the effects on probe signal (e.g., fluorescence) at various time points and temperatures (a first measurement time point at temperature T1, a second measurement time point at temperature T2, and a third measurement time point at temperature T3) is described in Table 1. Potentially, combinations of probe modifications can occur at the same time, but only the outcomes of single modifications are presented in the table. As discussed above, there are a number of possible ways that the integrity of a probe can be destroyed. However, those of skill in the art will recognize that probes can fail in additional ways, and therefore the following table should in no way be interpreted to limit the scope of the invention.

TABLE 1

Effects of probe modifications on signal intensities of probes.

| Failure | Description | Signal at T1 (Relative to Reference | Signal at T2 (Relative to Reference | Signal at T3 (Relative to Reference | Signal T2−T1 (Relative to Reference |
|---|---|---|---|---|---|
| 1 | Probe cleaved. This leads to destabilization of the stem structure and separation of the reporter and quencher. | ↑ | ↑ | ↑ | ↓ |
| 2 | Reporter is detached from probe. | ↑ | ↑ | ↑ | ↓ |
| 3 | Quencher is detached from probe. | ↑ | ↑ | ↑ | ↓ |
| 4 | Fluorescence of reporter is reduced | ↓ | ↓ | ↓ | ↓ |
| 5 | Quencher degraded. Capacity of quencher to quench fluorescence is reduced while the quencher is attached to the probe | ↑ | ↑ | ↑ | ↓ |
| 6 | Probe is hybridized to excess non-specific moieties present in the sample | No change | No change | ↑ | No change |

The assessment of probe integrity by this approach would be applicable when the probe is diluted in buffer, but could also apply when the probe is in another matrix, such as in a real-time PCR reaction mixture that contains a test sample, including, e.g., a patient sample. A typical reaction mixture contains, e.g., the test sample, 200 nM Molecular Beacons probe, Taq polymerase, 50 mM Tris, pH 8.3, 8 mM MgCl2, 200 μM dATP, 200 μM dTTP, 200 μM dCTP, 200 μM dGTP, 50 mM KCl, 200 nM forward primer and 200 nM reverse primer.

III. Linear Probes

The probe check assay can also be used to assess the integrity of a linear probe. Linear fluorescent probes, such as TaqMan probes, that are quenched by an attached quencher have an inherent 'background' fluorescence. This fluorescence can be used as an indicator of probe integrity, and by correlation, can be used as an indicator for the performance of the probe in a real-time PCR assay. Examples of modification to probes and the resultant effects on fluorescence are as follows in Table 2.

TABLE 2

Effects of probe modifications on signal intensities of probes.

| | Modification of probe | Effect on probe signal compared to a threshold value |
|---|---|---|
| 1 | Probe is cleaved. | Increased |
| 2 | Reporter is detached from probe. | Increased |
| 3 | Quencher is detached from probe. | Increased |
| 4 | Capability of quencher to quench fluorescence is reduced while the quencher is still attached to the probe | Increased |
| 5 | Fluorescence of reporter is reduced | Decreased |

Other probes useful in the methods of the invention include those probes that do not comprise a quenching agent, but which are quenched to some degree by the probe sequence itself. Such probes, for instance, can be linear or can comprise some secondary structure. One example of such probes are "Light-up" probes, which are peptide nucleic acid probes. See, e.g., Svanvik, N., et al. *Anal. Biochem.* 281:26–35 (2000); Svanvik, N., et al., *Anal Biochem.* 287:179–182 (2000).

IV. Threshold Values For Comparison to Probe Signal

As discussed above, an intact probe can be run side by side with a sample probe and then compared to the sample probe signal. However, for convenience and economy, in some preferred embodiments, the threshold value is a predetermined value or range. Predetermined values or ranges of values are determined from a succession of control experiments to define a typical signal of an intact probe. Following such an analysis, a standard range of values can be determined. These values can then be used to compare with sample probe signals in a probe check assay.

In some embodiments, the threshold value is calculated by determining a set of probe check values that correlate with acceptable PCR results. Mixtures of probes composed of various proportions of fully functional and degraded probes can be evaluated by both the probe check and PCR assays to measure the ability of the probe mixtures to accurately measure target quantities. In preferred embodiments, the threshold value is determined as the probe check value (i.e, signal) of the probe mixture that contains the highest proportion of degraded probe and retains an acceptable PCR performance. Those of skill in the art will recognize that the threshold value can be a single threshold value or an upper and lower limit.

Since there can be some imprecision in the probe check measurements, multiple assays can be performed to add statistical confidence to the correlation and threshold values. Moreover, to eliminate variation between probe check readings, the raw probe check values can be normalized. Those of skill in the art will recognize that any value associated with signal detection of a detection instrument can be used to normalized the probe check values. In preferred embodiments, a passive dye is run in the probe check sample and probe check value is normalized to the signal of the dye. Preferred dyes are substantially unaffected by the presence or association with nucleic acids, particularly double stranded DNA. Such dyes may include virtually any fluorescent dye fulfilling this criterion which is also spectrally resolvable. Preferred dyes include rhodamine dyes and fluorescein dyes. The passive reference could be in the same matrix as the probe or in a separate matrix, such as a separate reaction vessel. The passive reference could be free in solution or conjugated to a larger molecule such as an oligonucleotide or protein. Alternatively, stored values relating to calibration of the detection instrument can also be used as normalizing values.

For probes that change conformation and signal in response to temperature changes, threshold values can be determined at various temperatures (e.g., at temperatures below and above the self-annealing temperature of the probe when the probe is not bound to a target nucleic acid). In addition, the difference of signal of the probe between different temperatures is also useful. For example, the difference of signal at a temperature below and above the self-annealing temperature of the probe can be monitored using mixtures of probes comprising increasing amounts of degraded probe. See, e.g., Example 2. Signals of mixtures that produce acceptable results are then used as a threshold value.

Rather than relating the probe check assay results to predetermined limits, the fluorescence readings of a probe can be compared to a passive reference molecule that correlates with the signal of an intact probe. This correlation is then used as a means for assessing the integrity and functional performance of the probe. As an example, the fluorescent reading of the reference molecule is read at a specified temperature prior to or subsequent to determining the fluorescence of a probe. A relationship between the fluorescence of the probe and passive reference is determined and based on previous studies would be used to discriminate between fully functional probes and those that will not perform adequately in an assay.

Predetermined threshold values or ranges can be stored in a computer memory and accessed as necessary by a controller.

V. Alternatives to an External Control

The probe check assay, as described herein, in combination with a PCR internal control with shared primers, can replace an assay external positive control. Most assays, including amplification-based ones use control reactions to validate the assay. Typically, separate positive and negative controls are run in conjunction with the test reaction. The negative control is a test for possible contamination of the assay while the positive control is a test for the integrity and functional performance of the reaction components.

Internal controls are controls that are run in the same reaction as a test sample and test for the integrity of the reagent plus possible interference by the sample matrix (Rosenstraus, et al., *J. Clin. Microbiology* 36:191–197 (1998)). In some PCR reactions, the internal control target and assay specific target are amplified with the same primers, i.e. shared primers. In these reactions, the fluorescent probes for detecting the assay specific target and internal control are different.

For these assays, the results of a probe check assay and internal control can be used in place of an external positive control. The internal control validates the integrity of all the reagent components, including the primers, but not the integrity of the probes. The integrity and functional performance of the probes can be validated by performing a probe check assay, e.g., comparing the fluorescence values at least one of temperature T1, temperature T2 or temperature T3 to predetermined values. Thus, taken together, the results of the probe check assay and the PCR results for the internal control will define the integrity of all the PCR reagent components, thereby removing the need for an external positive control.

In some embodiments, the methods of the invention provide for the complete internalization of all controls. For example, in some embodiments, the probe check assay, as described herein, is used in combination with additional control templates in an amplification reaction to control for quality and quantity of assay components, enzyme activity, etc. In particular, an amplification reaction can comprise at least three polynucleotide sequences: a target template (T) and two control templates (IC1 and IC2). The two control templates function to control for the integrity of the amplification reaction. Amplification products of the target and of the control templates can be measured by quantifying probe binding to reaction products. Thus, each amplification product provides a target for at least one corresponding probe that is useful for detecting and quantifying the amplification products.

The invention provides a target template (T) that comprises a nucleic acid sequence with hybridization sites for a 5' and 3' target primer (P1 and P2, respectively). The target template (T) comprises a polynucleotide sequence that is sought to be amplified ("the target sequence"). This sequence, or a subsequence of this sequence, provides a hybridization sequence for a target probe (HP1).

The first control template (IC1) comprises the same target primer hybridization sequences (i.e., for P1 and P2) as the target template (T) and a probe hybridization sequence that is different from the target template. Thus, amplification of this template controls for the integrity of the general reaction, e.g., function of enzyme, reagents, target primers, etc. For example, if no target product is produced, but the first control template (IC1) is amplified in a reaction, this indicates that amplification conditions (buffer, temperature, primers, enzymes, etc.) were capable of amplifying a template. If the first control template (IC1) is not amplified, then it is likely that the reaction mixture was defective and therefore, a negative product from the template may not be due to lack of template.

The second control template (IC2) comprises hybridization sequences for the target probe (HP1) and a second control probe (HP3). These two sequences are flanked by hybridization sequences for a pair of second control primers (P3 and P4). Amplification of this template provides a control for binding of the target probe (HP1) to the target sequence. For example, if the second control probe (HP3) does not produce any signal, then it is likely that there was no amplification of the second control template (IC2). However, if the second control probe (HP3) produces signal but the target probe (HP1) does not, then it is likely that the target probe (HP1) has failed to function.

Because the second control template (IC2) has one copy each of the target probe hybridization sequence and the second control hybridization sequence, signal from the target probe (HP1) and the second control probe (HP3) should be substantially equal if the target template (T) is not present. If the target template (T) is present, then more target probe (HP1) hybridization sequences (i.e., target amplification products) should be available relative to second control probe (HP3) hybridization sequences. Thus, a properly functioning reaction should have higher signal from a target probe (HP1) than from the second control probe (HP3). This is particularly true in earlier amplification cycles. Therefore, in some embodiments, real time measurements of probe binding can be useful, e.g., for quantitative PCR.

Studies have shown that initial copy number can be quantified during real-time PCR analysis based on threshold cycle (Ct). See, Higuchi, R., et al. *Biotechnology* 11:1026–1030 (1993). Ct is defined as the cycle at which fluorescence is determined to be statistically significant above background. The cycle threshold is inversely proportional to the log of the initial copy number. The more template that is present to begin with, the fewer the number of cycles it takes to get to a point where the fluorescent signal is detectable above background. Quantitative information based on threshold cycle can be more accurate than information based on endpoint determinations because it is based on a measurement taken during the exponential phase of PCR amplification when the PCR efficiency has yet to be influenced by limiting reagents, small differences in reaction components, or cycling conditions.

Table 3 demonstrates how the cycle threshold values are useful to determine the integrity of a particular reaction. The table provides hypothetical Ct values depending on different reaction scenarios.

TABLE 3

Interpretation of Real-Time PCR Results Based on Cycle Threshold Values of Hybridization Probes 1, 2, and 3

| Sample | HP1: (target and IC2) | HP2: (IC1) | HP3: (IC2) | Test Result |
|---|---|---|---|---|
| Negative, non-inhibiting | Same as HP3. Ct is less than or equal to Y | Ct is less than or equal to X | Same as HP1. Ct is less than or equal to Y | Negative |
| High positive, non-inhibiting | Ct is significantly less than HP3 by a factor of z | No Ct value or Ct is less than or equal to X | No cycle threshold or Ct is greater than HP1 and less than or equal to Y | Positive |
| Low positive, non-inhibiting | Ct is less than HP3 | Ct is less than or equal to X | Ct is greater than HP1 and less than or equal to Y | Positive |
| Reagent degradation | No Ct value | No Ct value | No Ct value | Invalid |

TABLE 3-continued

Interpretation of Real-Time PCR Results Based on Cycle Threshold Values of Hybridization Probes 1, 2, and 3

| Sample | HP1: (target and IC2) | HP2: (IC1) | HP3: (IC2) | Test Result |
|---|---|---|---|---|
| Negative, inhibitors present in sample | No Ct value or Ct is equal to HP3 | No Ct value or Ct is greater than X or low fluorescent endpoint value | No Ct values or Ct is greater than Y or low fluorescent endpoint value | Invalid |
| Positive, inhibitors present in sample | Ct is less than HP3 | Ct is greater than X or low fluorescent endpoint value | Ct is greater than Y or low fluorescent endpoint value | Positive result; unable to quantify due to inhibitors |

z = factor defining separation between HP1 and HP3 Ct values
X = maximum Ct value for a valid result for Probe 2 (IC1)
Y = maximum Ct value for a valid result for Probe 3 (IC2)

VI. Amplification Reactions and Thermal Processing Instruments

Amplification of an RNA or DNA template using reactions is well known (see U.S. Pat. Nos. 4,683,195 and 4,683,202; PCR Protocols: *A Guide to Methods and Applications* (Innis et al., eds, 1990)). Methods for amplifying and detecting nucleic acids by PCR using a thermostable enzyme are disclosed in U.S. Pat. No. 4,965,188, which is incorporated herein by reference. PCR amplification of DNA involves repeated cycles of heat-denaturing the DNA, annealing two oligonucleotide primers to sequences that flank the DNA segment to be amplified, and extending the annealed primers with DNA polymerase. The primers hybridize to opposite strands of the target sequence and are oriented so that DNA synthesis by the polymerase proceeds across the region between the primers, effectively doubling the amount of the DNA segment. Moreover, because the extension products are also complementary to and capable of binding primers, each successive cycle essentially doubles the amount of DNA synthesized in the previous cycle. This results in the exponential accumulation of the specific target fragment, at a rate of approximately 2n per cycle, where n is the number of cycles.

Methods such as polymerase chain reaction (PCR) and ligase chain reaction (LCR) can be used to amplify nucleic acid sequences of target DNA sequences directly from mRNA, from cDNA, from genomic libraries or cDNA libraries. The reaction is preferably carried out in a thermal processing instrument to facilitate incubation times at desired temperatures. The thermal processing instruments can also optionally comprise at least one detection mechanism for detecting nucleic acid sequences of interest. Preferred thermal processing instruments include the Smart Cycler® (Cepheid, Sunnyvale, Calif.) as well as those described in, e.g., WO 99/60380. Other suitable instruments are described, e.g., in, U.S. Pat. Nos. 5,958,349; 5,656,493; 5,333,675; 5,455,175; 5,589,136 and 5,935,522.

Isothermic amplification reactions are also known and can be used according to the methods of the invention. Examples of isothermic amplification reactions include strand displacement amplification (SDA) (Walker, et al. *Nucleic Acids Res.* 20(7): 1691–6 (1992); Walker *PCR Methods Appl* 3(1):1–6 (1993)), transcription-mediated amplification (Phyffer, et al., *J. Clin. Microbiol.* 34:834–841 (1996); Vuorinen, et al. , *J. Clin. Microbiol.* 33:1856–1859 (1995)), nucleic acid sequence-based amplification (NASBA) (Compton, *Nature* 350(6313):91–2 (1991), rolling circle amplification (RCA) (Lisby, *Mol. Biotechnol.* 12(1):75–99 (1999)); Hatch et al., *Genet. Anal.* 15(2):35–40 (1999)) and branched DNA signal amplification (bDNA) (see, e.g., Iqbal et al., *Mol. Cell Probes* 13(4):315–320 (1999)). Other amplification methods known to those of skill in the art include CPR (Cycling Probe Reaction), SSR (Self-Sustained Sequence Replication), SDA (Strand Displacement Amplification), QBR (Q-Beta Replicase), Re-AMP (formerly RAMP), RCR (Repair Chain Reaction), TAS (Transcription Based Amplification System), and HCS.

The methods for determining the integrity of a probe are particularly useful to analyze products of amplification reactions, including quantitative PCR and/or real time amplification reactions. Several methods have been described for the quantitative analysis of nucleic acid sequences. The polymerase chain reaction (PCR) and reverse-transcriptase PCR (RT-PCR) permit the analysis of small starting quantities of nucleic acid (e.g., as little as one cell equivalent).

Another method, quantitative competitive PCR (QC-PCR), has been developed and used widely for PCR quantitation. QC-PCR relies on the inclusion of a known amount of an internal control competitor in each reaction mixture. To obtain relative quantitation, the unknown target PCR product is compared with the known competitor PCR product. The relative amount of target-specific and competitor DNA is measured, and this ratio is used to calculate the starting number of target templates. The larger the ratio of target specific product to competitor specific product, the higher the starting DNA concentration. Success of a QC-PCR assay relies on the development of an internal control that amplifies with the same efficiency as the target molecule. In the QC-PCR method of RNA quantitation, a competitive RNA template matched to the target sequence of interest, but different from it by virtue of an introduced internal deletion, is used in a competitive titration of the reverse transcription and PCR steps, providing stringent internal control. Increasing amounts of known copy numbers of competitive template are added to replication portions of the test sample, and quantitation is based on determination of the relative (not absolute) amounts of the differently sized amplified products derived from the wild-type and competitive templates.

The methods of the invention can be used in traditional multiplex reactions. Multiplex PCR results in the amplification of multiple polynucleotide fragments in the same reaction. See, e.g., PCR Primer, A Laboratory Manual (Dieffenbach, ed. 1995) Cold Spring Harbor Press, pages 157–171. For instance, different target templates can be added and amplified in parallel in the same reaction vessel.

VII. Probes

Probes of the invention are capable of hybridizing to a particular polynucleotide sequence. Thus probes of the invention can comprise a polynucleotide sequence that is complementary to the sequence to be detected. In some embodiments, the probe also comprises a fluorophore or enzyme, as described below, which allows for the detection of the binding of the probe to its complement.

Probe concentration should be sufficient to bind to the amount of target or control sequences that are amplified so as to provide an accurate assessment of the quantity of amplified sequence. Those of skill in the art will recognize that the amount of concentration of probe will vary according to the binding affinity of the probe as well as the quantity of sequence to be bound. Typical probe concentrations will range from 0.01 μM to 0.5 μM.

The present invention can employ many different nucleic acid hybridization probes. Typically, for signal generation, the probes utilize a change in the fluorescence of a fluorophore due to a change in its interaction with another molecule or moiety brought about by changing the distance between the fluorophore and the interacting molecule or moiety.

These assays rely for signal generation on fluorescence resonance energy transfer, or "FRET", according to which a change in fluorescence is caused by a change in the distance separating a first fluorophore from an interacting resonance energy acceptor, either another fluorophore or a quencher. Combinations of a fluorophore and an interacting molecule or moiety, including quenching molecules or moieties, are known as "FRET pairs." The mechanism of FRET-pair interaction requires that the absorption spectrum of one member of the pair overlaps the emission spectrum of the other member, the first fluorophore. If the interacting molecule or moiety is a quencher, its absorption spectrum must overlap the emission spectrum of the fluorophore. Stryer, L., *Ann. Rev. Biochem.* 47: 819–846 (1978); BIOPHYSICAL CHEMISTRY part II, Techniques for the Study of Biological Structure and Function, C. R. Cantor and P. R. Schimmel, pages 448–455 (W. H. Freeman and Co., San Francisco, U.S.A., 1980); and Selvin, P. R., *Methods in Enzymology* 246: 300–335 (1995). Efficient FRET interaction requires that the absorption and emission spectra of the pair have a large degree of overlap. The efficiency of FRET interaction is linearly proportional to that overlap. See Haugland, R. P. et al. *Proc. Natl. Acad. Sci. USA* 63: 24–30 (1969). Typically, a large magnitude of signal (i.e., a high degree of overlap) is required. FRET pairs, including fluorophore-quencher pairs, are therefore typically chosen on that basis.

One suitable FRET pair disclosed in Matayoshi et al. 1990, *Science* 247: 954–958, includes DABCYL as a quenching moiety (or quenching label) and EDANS as a fluorophore (or fluorescent label). The absorption spectrum of DABCYL has a high degree of overlap with the emission spectrum of EDANS, making these two a good FRET pair.

A variety of labeled nucleic acid hybridization probes and detection assays that utilize FRET and FRET pairs are known. One such scheme is described by Cardullo et al. *Proc. Natl. Acad. Sci. USA* 85: 8790–8794 (1988) and in Heller et al. EP 0070685. It uses a probe comprising a pair of oligodeoxynucleotides complementary to contiguous regions of a target DNA strand. One probe molecule contains a fluorescent label, a fluorophore, on its 5' end, and the other probe molecule contains a different fluorescent label, also a fluorophore, on its 3' end. When the probe is hybridized to the target sequence, the two labels are brought very close to each other. When the sample is stimulated by light of an appropriate frequency, fluorescence resonance energy transfer from one label to the other occurs. FRET produces a measurable change in spectral response from the labels, signaling the presence of targets. One label could be a "quencher," which in this application is meant an interactive moiety (or molecule) that releases the accepted energy as heat.

Another solution-phase scheme utilizes a probe comprising a pair of oligodeoxynucleotides and a FRET pair. However, here the two probe molecules are completely complementary both to each other and to complementary strands of a target DNA (Morrison and Stols, *Biochemistry* 32: 309–3104 (1993) and Morrison EP 0 232 967 A2. Each probe molecule includes a fluorophore conjugated to its 3' end and a quenching moiety conjugated to its 5' end. When the two oligonucleotide probe molecules are annealed to each other, the fluorophore of each is held in close proximity to the quenching moiety of the other. With the probe in this conformation, if the fluorophore is then stimulated by light of an appropriate wavelength, the fluorescence is quenched by the quenching moiety. However, when either probe molecule is bound to a target, the quenching effect of the complementary probe molecule is absent. In this conformation a signal is generated. The probe molecules are too long to self-quench by FRET when in the target-bound conformation.

A solution-phase scheme that utilizes FRET pairs and the phenomenon known as strand displacement is described by Diamond et al., U.S. Pat. No. 4,766,062; Collins et al. U.S. Pat. No. 4,752,566; Fritsch et al. U.S. Pat. Nos. 4,725,536 and 4,725,537. Typically, these assays involve a probe comprising a bimolecular nucleic acid complex. A shorter single strand comprising a subset of the target sequence is annealed to a longer single strand that comprises the entire target binding region of the probe. The probe in this configuration thus comprises both single-stranded and double-stranded portions. These probes may further comprise either a $^{32}P$ label attached to the shorter strand or a fluorophore and a quencher moiety which could be held in proximity to each other when the probe conformation is that complex. Another type of molecular probe assay utilizing a FRET pair is described in European Patent Application 0 601 889 A3.

Another type of nucleic acid hybridization probe assay utilizing a FRET pair is the "TaqMan®" assay described in Gelfand et al. U.S. Pat. No. 5,210,015, and Livak et al. U.S. Pat. No. 5,538,848. The probe is a single-stranded oligonucleotide labeled with a FRET pair. In a TaqMan® assay, a DNA polymerase releases single or multiple nucleotides by cleavage of the oligonucleotide probe when it is hybridized to a target strand. That release provides a way to separate the quencher label and the fluorophore label of the FRET pair.

Yet another type of nucleic acid hybridization probe assay utilizing FRET pairs is described in Tyagi et al. U.S. Pat. No. 5,925,517, which utilizes labeled oligonucleotide probes, which are referred to as "Molecular Beacons." See Tyagi, S. and Kramer, F. R., *Nature Biotechnology* 14: 303–308 (1996). A Molecular beacon probe is an oligonucleotide whose end regions hybridize with one another in the absence of target but are separated if the central portion of the probe hybridizes to its target sequence. The rigidity of the probe-target hybrid precludes the simultaneous existence of both the probe-target hybrid and the intramolecular hybrid formed by the end regions. Consequently, the probe undergoes a conformational change in which the smaller hybrid formed by the end regions disassociates, and the end regions are separated from each other by the rigid probe-target hybrid. For molecular beacon probes, a central target-recognition sequence is flanked by arms that hybridize to one another when the probe is not hybridized to a target strand, forming a "hairpin" structure, in which the target-recognition sequence (which is commonly referred to as the "probe sequence") is in the single-stranded loop of the hairpin structure, and the arm sequences form a double-stranded stem hybrid. When the probe hybridizes to a target, that is, when the target-recognition sequence hybridizes to a complementary target sequence, a relatively rigid helix is formed, causing the stem hybrid to unwind and forcing the arms apart.

Quenching molecules and even other fluorophores can serve as efficient quenching moieties for fluorophores when attached to nucleic acid hybridization probes such that the fluorescing moiety and quenching moiety are in contact, even when the rules of FRET are violated. Further, the absorption spectra of a pair of chromophores (fluorescing or non-fluorescing), even identical chromophores, in a probe so constructed is altered in a detectable fashion.

In FRET, a first fluorophore absorbs at a first wavelength and emits at a second, longer wavelength. A second chromophore (i.e. either a fluorophore or a quencher) which is near the first (the FRET range is reportedly 10–100 Å) and to the degree its absorption spectrum overlaps that emission, absorbs some or most of the emitted energy. If the second chromophore is a fluorophore, the chromophore re-emits at a third, still longer wavelength. Alternatively, if the chromophore is a quencher, the chromophore releases the energy as heat. FRET progresses in the direction of increasing wavelength.

Non-FRET fluorescent probes are also encompassed by the invention. See, e.g., Tyagi et al., U.S. Pat. No. 6,150,097 ("the '097 patent"). For example, the '097 patent describes how changes in the absorption spectra of the label pair can be used as a detectable signal as an alternative to change in fluorescence. When change in absorption is utilized, the label pair may include any two chromophores, that is, fluorophores, quenchers and other chromophores. The label pair may even be identical chromophores.

VIII. Quantification of Probe Binding

Binding of a probe to its complementary hybridization sequence allows the user to quantify the accumulation of a particular sequence without necessarily removing the contents from the reaction vessel. In general, any type of label that allows for the detection and differentiation of different probes can be used according to the methods of the invention.

Accumulation of amplified product can be quantified by any method known to those in the art. For instance, fluorescence from a probe can be detected by measurement of light at a particular frequency. Similarly, the accumulation of various chemical products created via an enzymatic reaction linked to the probe can be measured, for instance, by measuring absorbance of light at a particular wavelength. In other embodiments, amplification reactions can be quantified directly by blotting them onto a solid support and hybridizing with a radioactive nucleic acid probe. Once unbound probe is washed away, the amount of probe can be quantified by measuring radioactivity as is known to those of skill in the art. Other variations of this technique employ the use of chemiluminescence to detect hybridization events.

Measurement of amplification products can be performed after the reaction has been completed or can be measured in "real time" (i.e., as the reaction occurs). If measurement of accumulated amplified product is performed after amplification is complete, then detection reagents (e.g. probes) can be added after the amplification reaction. Alternatively, probes can be added to the reaction prior or during the amplification reaction, thus allowing for measurement of the amplified products either after completion of amplification or in real time. Real time measurements are preferred because they allow for measurement at any given cycle of the reaction and thus provide more information about accumulation of products throughout the reaction. For measurement of amplification product in real time, the use of fluorescent probes is preferred.

One of skill will recognize that a large number of different fluorophores can be used. Some fluorophores useful in the methods and composition of the invention include: fluorescein, fluorescein isothiocyanate (FITC), carboxy tetrachloro fluorescein (TET),NHS-fluorescein, 5 and/or 6-carboxy fluorescein (FAM), 5- (or 6-) iodoacetamidofluorescein, 5-{[2(and 3)-5-(Acetylmercapto)-succinyl]amino} fluorescein (SAMSA-fluorescein), and other fluorscein derivatives, rhodamine, Lissamine rhodamine B sulfonyl chloride, Texas red sulfonyl chloride, 5 and/or 6 carboxy rhodamine (ROX) and other rhodamine derivatives, coumarin, 7-amino-methyl-coumarin, 7-Amino-4-methylcoumarin-3-acetic acid (AMCA), and other coumarin derivatives, BODIPY™ fluorophores, Cascade Blue™ fluorophores such as 8-methoxypyrene-1,3,6-trisulfonic acid trisodium salt, Lucifer yellow fluorophores such as 3,6-Disulfonate-4-amino-naphthalimide, phycobiliproteins derivatives, Alexa fluor dyes (available from Molecular Probes, Eugene, Oreg.) and other fluorophores known to those of skill in the art. For a general listing of useful fluorophores, see Hermanson, G. T., BIOCONJUGATE TECHNIQUES (Academic Press, San Diego, 1996). Thus, each probe will fluoresce at a different wavelength and can be individually detected without interference from the other probes.

IX. Normalization of Probe Signals

The invention also provides for the use of the probe check assay to normalize hybridization signals, including, e.g., readings during real-time amplification. The signal output of a probe is normalized to reduce variations between readings in a mixture or between mixtures. For instance, all optical systems, including real-time PCR systems, have reaction site to reaction site variation that complicate the comparison of results between sites. Previously described methods used to compensate for these differences include 'normalizing' the readings for each site by including a passive reference dye in the reaction mixture. See, e.g., U.S. Pat. No. 5,736,333.

However, instead of using a separate dye for normalizing the probe signals, the inherent "background" signal of the probes can be used for normalizing amplification growth curves. Before a PCR or other amplification reaction is started, an initial signal (e.g., fluorescence) of the probe is measured. This initial signal value is then used to normalize the target signal values of the probe obtained during amplification (i.e., to normalize the signal values measured when the probe is hybridized to a target nucleic acid). See, e.g., FIG. 8. Each target signal value of the probe can be normalized to the initial signal value of the probe in a number of ways, including by multiplying the target signal value of the probe by a scaling factor representing the initial signal value or by using linear transformations based on the initial signal value. In some preferred embodiments, the target signal values are normalized by dividing each target signal value by the initial signal value. Normalization may be applied to reactions that employ probe signals including, e.g., linear fluorescent probes (e.g. TaqMan®) and fluorescent probes that are quenched when self-annealed.

In addition, with respect to probes that change conformations in response to temperature changes (e.g., Molecular Beacons), the initial signal value of the probe may be measured either at temperature T1 below or equal to the self-annealing temperature of the probe, or at temperature T2 above the self-annealing temperature of the probe, or at temperature T3 below or equal to the self-annealing temperature of the probe. This initial signal value of the probe measured at either temperature T1, temperature T2, or temperature T3 is then used to normalize the subsequent target signal values of the probe measured when the probe is hybridized to a target nucleic acid. In another preferred embodiment of the invention, the difference between two initial signal values measured at different temperatures is used as the normalizing factor. See, e.g., FIGS. 9 and 10. For example, the difference between the initial probe signal at temperature T2 and temperature T1 or the difference between the initial probe signals at temperature T2 and temperature T3 can be used as a normalizing factor to normalize the target signal values. See, e.g., Example 3.

Figure 8:
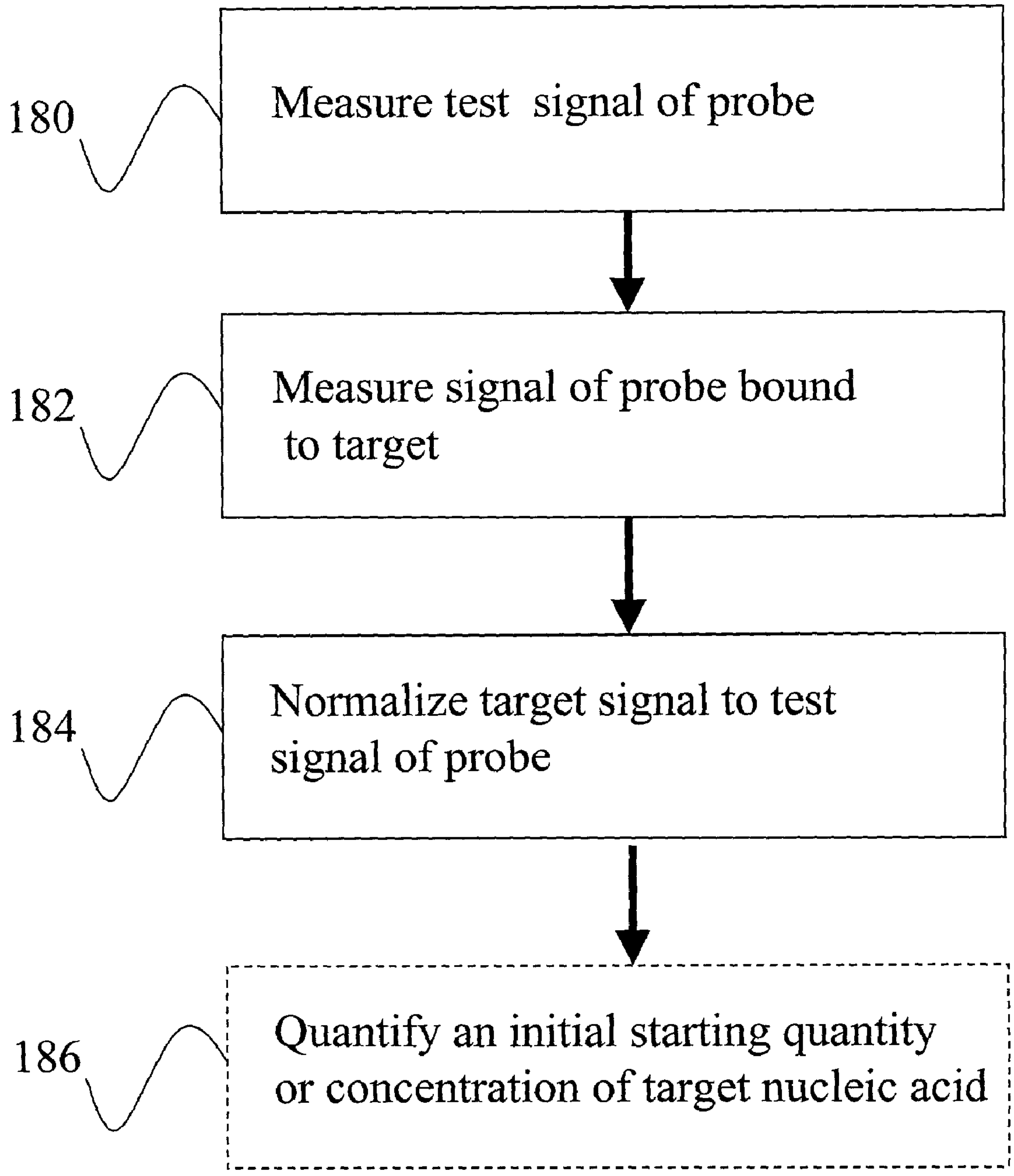
FIG. 8 is a flowchart illustrating some embodiments of the methods of normalizing the target signal of a probe to a test signal of a probe.
Figure 9:
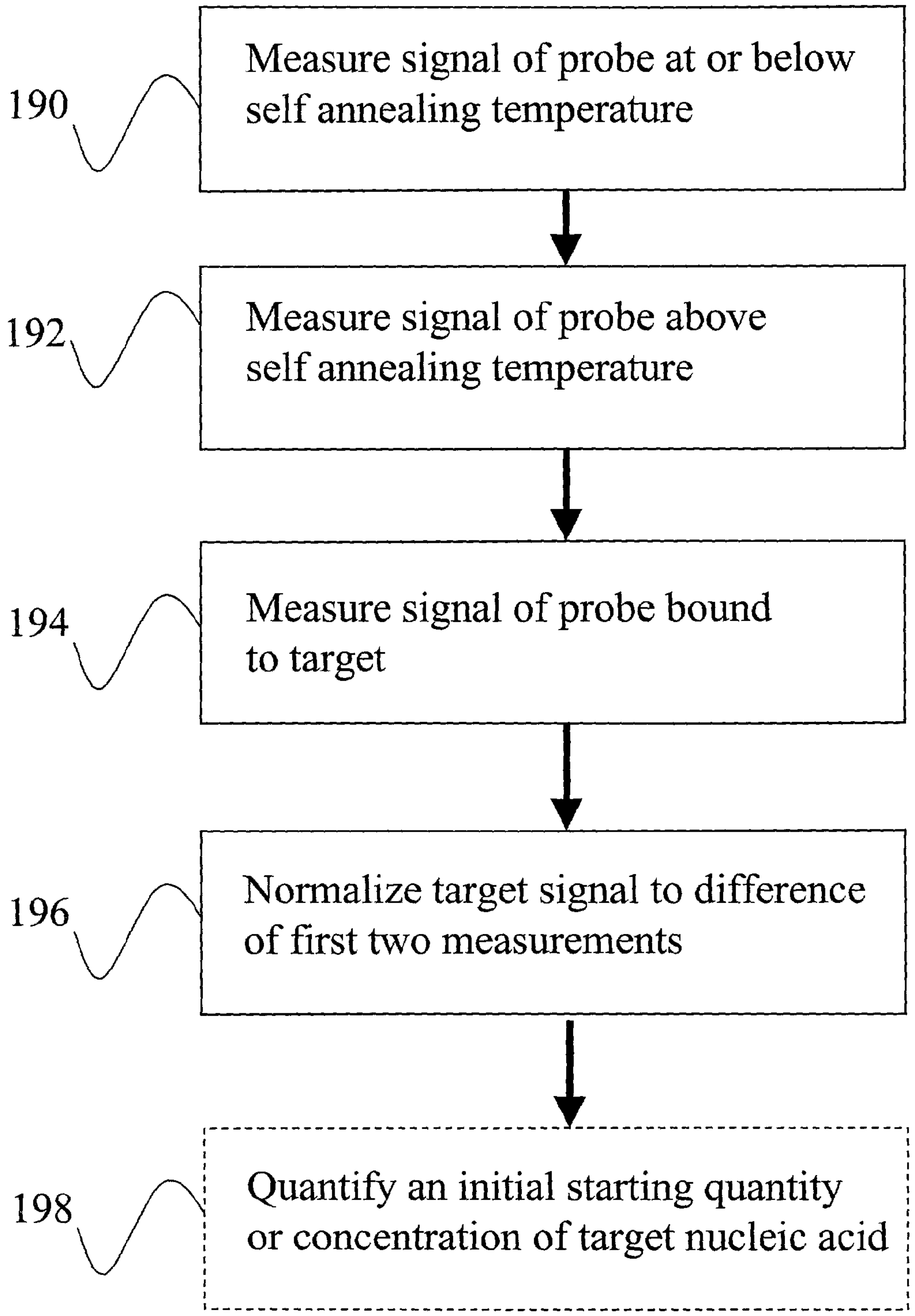
FIG. 9 is a flowchart illustrating some embodiments of the methods of normalizing the target signal of a probe.
Figure 10:
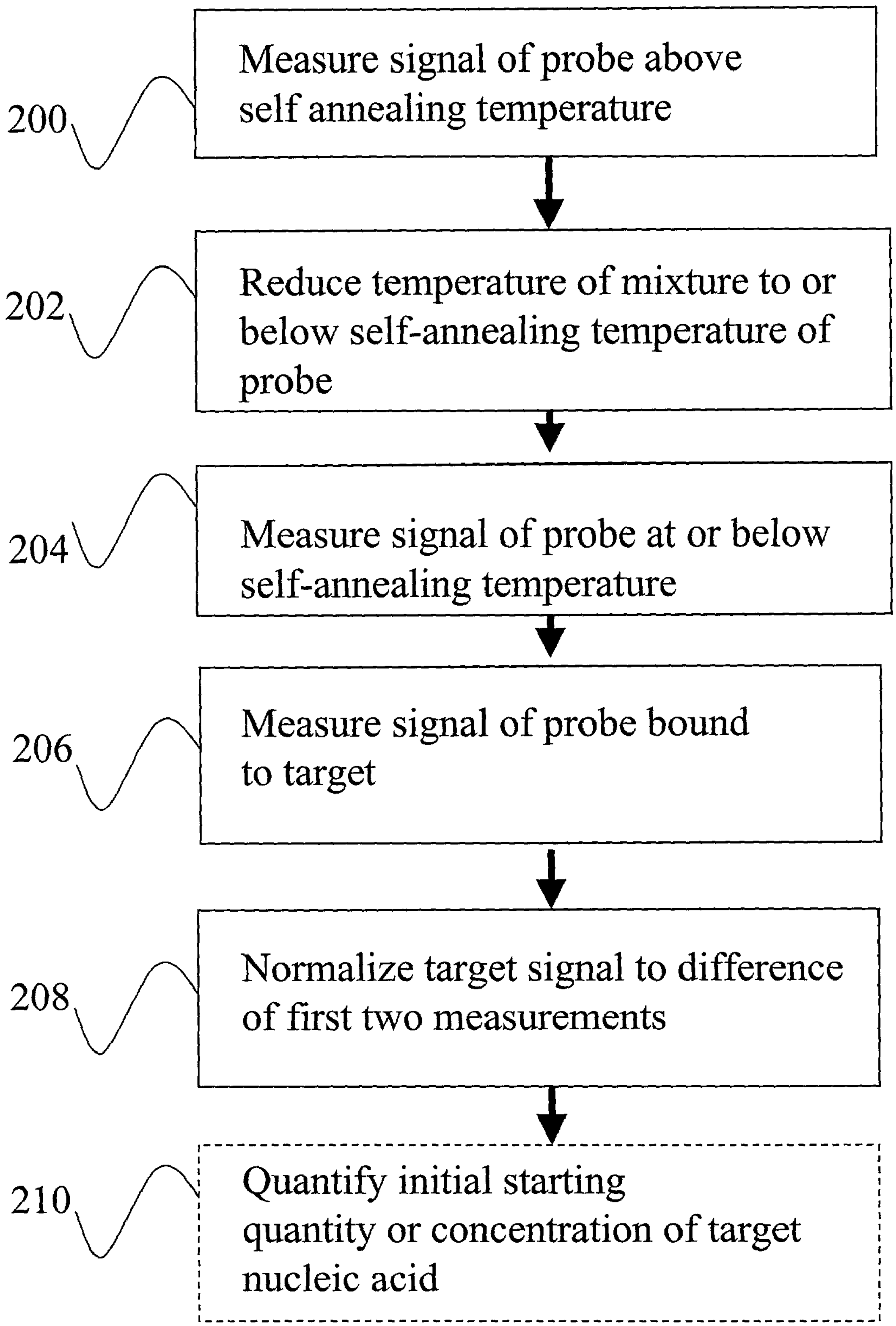
FIG. 10 is a flowchart illustrating some embodiments of the methods of normalizing the target signal of a probe.

The normalized signal values described above are useful for quantitative analysis. In some aspects of the invention, the initial starting quantity or concentration of a target nucleic acid is determined using the normalized signal values. FIGS. 8–10 illustrate embodiments of the invention where the normalized target signal is optionally used to quantify an initial quantity or concentration of a target nucleic acid. Determination of a starting quantity typically involves first developing a calibration curve using two or more standards (e.g., at least two different known starting quantities of a calibration nucleic acid sequence). The calibration curve relates threshold cycle number to the log of starting quantity or concentration. See, e.g., EP 0640828, Orlando et al., *Clin. Chem. Lab. Med.* 36(5):255–69 (1998); Gililand, G. et al., *Proc. Natl. Acad. Sci. USA,* 87:2725–2729 (1990). According to one aspect of the present invention, an initial starting quantity or concentration of a target nucleic acid sequence is determined by calculating normalized signal values for the target sequence as described above, determining a threshold cycle number for the target nucleic acid sequence using the normalized signal values, and inserting the threshold cycle number into the equation of the calibration curve to yield the initial starting quantity Studies have shown that initial copy number can be quantified during real-time PCR analysis based on threshold cycle. See, Higuchi, R., et al. *Biotechnology* 11:1026–1030 (1993). Threshold cycle is defined as the cycle at which fluorescence is determined to be statistically significant above background. The threshold cycle is inversely proportional to the log of the initial copy number. The more template that is present to begin with, the fewer the number of cycles it takes to get to a point where the fluorescent signal is detectable above background. According to another aspect of the present invention, the calibration curve relating threshold cycle number to the log of the initial copy number may also be derived using normalized signal values of the at least two standards. For example, an initial signal value (or difference between initial signal values measured at two different temperatures) is measured for each of the two or more standards used to derive the calibration curve. The subsequent signals measured for each of these standards during amplification are then normalized to the respective initial signal value (or difference between initial signal values) measured for the standard. The normalized threshold values for each standard may then be used to determine a threshold cycle number for the standard. Once a threshold cycle number is determined for each standard, a calibration curve is derived from the threshold cycle numbers and known starting quantities of the standards. This calibration curve may be used to determine a starting quantity of concentration of a target nucleic acid in a sample, as described above. The standards used to derive the calibration curve may be amplified in the same reaction vessel with the target nucleic acid sequence (internal standards) or in a separate amplification reaction (external standards). Although quantification techniques that employ threshold cycle numbers are presently preferred, it is also possible to quantify the initial starting quantity or concentration of a target nucleic acid using endpoint analysis of the normalized signal values.

X. Apparatuses of the Invention

The present invention provides apparatuses that are useful for performing the methods of the invention. According to some embodiments, the invention provides an apparatus for testing the integrity of at least one probe for the detection of a nucleic acid, wherein the probe, when introduced into an amplification reaction, detects the accumulation of a nucleic acid by emitting a signal. The apparatus comprises at least (a) a temperature control system for changing the temperature of the reaction mixture; (b) at least one detection mechanism for measuring the fluorescence of the at least one probe; and (c) a controller in communication with the temperature control system and the detection mechanism. In some embodiments, the controller is programmed to perform the steps of: (i) measuring the signal of the probe at one or more time point; and (ii) determining the integrity of the probe by comparing the signal of the probe at the one or more time points with at least one threshold value.

In some embodiments, the detection mechanism detects fluorescence. Detection systems generally comprise a photomultiplier tube, CCD, photodiode, or other known detector. In the preferred embodiment, each detector is a PIN photodiode. See, e.g., PCT WO 99/60380. Suitable detection mechanisms for use in the apparatus and methods of the present invention include detection mechanisms that measure signals detectable by fluorescence, radioactivity, colorimetry, X-ray diffraction or absorption, magnetism, or enzymatic activity. Suitable labels for labeling nucleic acid sequences include, for example, fluorophores, chromophores, radioactive isotopes, electron-dense reagents, enzymes, and ligands having specific binding partners (e.g., biotin-avidin). Another suitable detection mechanism for use in the present invention detects and measures one or more electrical signals (e.g., measurements of electrical conductance, inductance, resistance, or capacitance) indicative of the quantity or concentration of a nucleic acid sequence.

In addition, in some embodiments, the controller is programmed to measure the fluorescence of the probe at two or more time points selected from the group of a first, second and third time point, wherein the temperature of the mixture is at or below the self-annealing temperature of the probe at the first time point, the temperature of the mixture is above the self-annealing temperature of the probe at the second time point, and the temperature of the mixture is at or below the self-annealing temperature of the probe at the third time point. Similarly, the detecting step can comprise comparing the fluorescence of the probe at two or more time points with two or more threshold values. In some embodiments, the controller signals the temperature control system to change the temperature of the reaction mixture.

In some embodiments, the controller is programmed to alter the temperature of a reaction mixture. For example, the controller can signal the temperature control system to cool the temperature of the reaction mixture to a temperature less than or equal to the self-annealing temperature of the probe prior to the first time point and between the second and third time point and to raise the temperature of the reaction mixture above the self-annealing temperature of the probe between the first and second time points.

In other embodiments, an apparatus for normalizing the fluorescence of at least one probe to quantify a polynucleotide in a sample is provided. In some embodiments, the probe is capable of hybridizing with a target nucleic acid molecule and the probe comprising a fluorophore and a quenching agent, wherein heating the probe causes the probe to change conformation from a first conformation to a second conformation, thereby changing the distance between the fluorophore and the quenching agent such that the fluorescence of the fluorophore is quenched or altered in the first conformation compared to the fluorescence of the fluorophore in the second conformation. The apparatus comprises, e.g., (a) at least one detection mechanism for measuring the fluorescence of the probe; and (b) a controller in communication with the detection system. The controller, for example, is programmed to perform the steps comprising (i) measuring a first fluorescence value of the probe at or below the self-annealing temperature of the probe, a second fluorescence value of the probe above the self-annealing temperature of the probe, and a target fluorescence value of the probe bound to a target polynucleotide. The controller can be further programmed to normalize the target fluorescence value using any of the normalization techniques previously described, e.g., by dividing the target fluorescence value by the difference of the second fluorescence value and the first fluorescence value.

As noted above, some probes useful in the methods of the invention change conformation in response to temperature and while other probes useful in the invention do not change conformation in response to temperature. For example, probes useful in the methods of the invention include molecular beacons as well as Taqman® probes. For such probes, the controller can be programmed to signal the detector to measure one signal of the probe. In these embodiments, the controller in communication with the detection system is programmed to perform the steps comprising measuring a test signal value of the probe, measuring a target signal value of the probe bound to a target polynucleotide; and normalizing the target signal value by dividing the target fluorescence value by the test signal value of the probe.

In some of the above-listed embodiments, the apparatus further comprises a temperature control system for raising the temperature of the reaction mixture above a self-annealing temperature of the probe and for cooling the temperature of the reaction mixture to a temperature less than or equal to the self-annealing temperature of the probe.

XI. Computer Program Products of the Invention

The present invention provides computer program products that are useful for performing the methods of the invention. In some embodiments, the present invention provides a computer program product readable by a machine comprising at least one detection mechanism for measuring at one or more time points a signal of at least one probe for the detection of a nucleic acid sequence, and comprising a temperature control system for changing the temperature of a reaction mixture containing the probe. The computer program product embodies a program of instructions executable by the machine to perform the steps comprising measuring the signal of the probe at one or more time point, and determining the integrity of the probe by comparing the fluorescence of the probe at the one or more time points with at least one threshold value. In some embodiments, the signal produced by the probe is fluorescence.

In some embodiments, the computer readable product receives data corresponding to the signal of the probe via a detection mechanism. At least one threshold value is then obtained, either from a detection system or by retrieving the threshold value from memory.

In some embodiments, the program of instructions comprises (a) measuring the fluorescence of the probe at two or more time points selected from the group consisting of a first, second and third time point, wherein the temperature of the mixture is at or below the self-annealing temperature of the probe at the first time point, the temperature of the mixture is above the self-annealing temperature of the probe at the second time point, and the temperature of the mixture is at or below the self-annealing temperature of the probe at the third time point; and (b) determining the integrity of the probe by comparing the fluorescence of the probe at the two or more time points with two or more threshold values. In some of these embodiments, the program of instructions further comprises the step of raising the temperature of the reaction mixture above the self-annealing temperature of the probe and subsequently cooling the temperature of the reaction mixture to a temperature less than or equal to the self-annealing temperature of the probe.

In some embodiments, the determining step comprises comparing either (a) the difference of fluorescence of the probe at the first and second time points with the threshold value or (b) the difference of fluorescence of the probe at the second and third time points with the threshold value.

As described herein, the threshold value is typically based on the signal of an intact probe. In addition, the program of instructions can comprise a step of determining the integrity of at least two different probes in the reaction mixture, the probes being capable of binding to different nucleic acid sequences.

In another aspect of the invention, a computer program is provided that executes the steps of (a) measuring a first fluorescence value of the probe at or below the self-annealing temperature of the probe; (b) measuring a second fluorescence value of the probe above the self-annealing temperature of the probe; (c) measuring a target fluorescence value of the probe bound to a target polynucleotide; and (d) normalizing the target fluorescence value to the target fluorescence value by the difference of the second fluorescence value and the first fluorescence value. The computer program product can normalize the target fluorescence value using any of the normalization techniques previously described, e.g., by dividing the target fluorescence value by the difference of the second fluorescence value and the first fluorescence value. Typically, the machine further comprises a temperature control system for raising the temperature of a reaction mixture containing the probe above a self-annealing temperature of the probe and for cooling the temperature of the reaction mixture to a temperature less than or equal to the self-annealing temperature of the probe. In addition, in some embodiments, the program of instructions comprises the steps of raising the temperature of a reaction mixture containing the probe above a self-annealing temperature of the probe and for cooling the temperature of the reaction mixture to a temperature less than or equal to the self-annealing temperature of the probe.

In addition, the computer program can embody a program of instructions executable by the machine to perform the steps comprising (a) measuring a test signal value of the probe; (b) measuring a target signal value of the probe bound to a target polynucleotide; and (c) normalizing the target signal value by dividing the target signal value by the test signal value of the probe. For example, the computer program product can normalize the target signal value using any of the normalization techniques previously described, e.g., by dividing the target signal value by the test signal value.

EXAMPLE

The following examples are offered to illustrate, but not to limit the claimed invention.

Example 1

This example illustrates a method for assessing the integrity of fluorescent probes that are quenched when self-annealed by comparing the fluorescence intensities of the probes to predetermined values.

Figure 11:
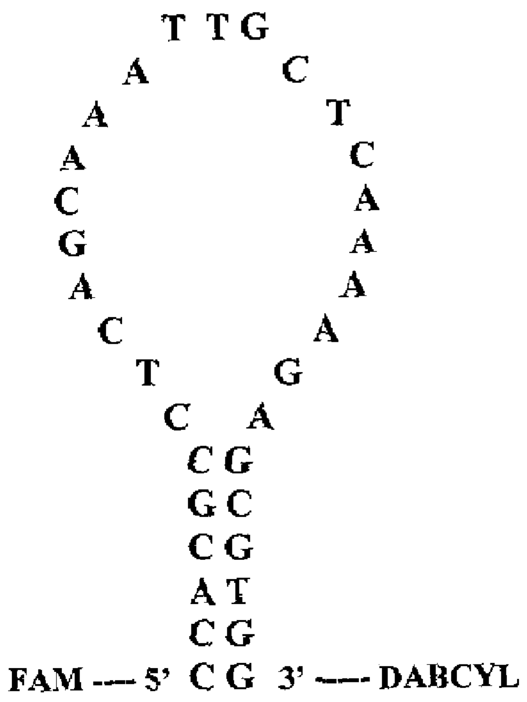
FIG. 11 illustrates an example of a molecular beacon probe.

A Molecular Beacon probe is labeled at the 5'-end with FAM as a reporter and at the 3'-end with a non-fluorescent quencher DABCYL. The 6 nucleotides internal from the 5'-end are homologous with the 6 nucleotides at the 3'-end. At low enough temperatures and in the presence of sufficient salt, these sequences hybridize to form a "stem" structure and the beacon forms a hairpin structure that brings the fluorescent reporter and quencher into close proximity (FIG. 11). This leads to a quenching of the fluorescence reporter.

The integrity of the probe can be determined by reading the fluorescence intensity of the probe at one or more temperatures. At a temperature below the melting temperature (Tm) of the stem sequence and in the presence of an adequate salt concentration, the fluorescence will be low because the reporter will be quenched. Depending on the temperature, raising the temperature will partially or fully denature the stem sequence and lead to an increase in fluorescence.

When compared to the results for intact fully functional probes, the fluorescence readings of a test probe can provide some insight into the integrity of the probe. A correlation can be established between the fluorescence readings and the functional performance of the probe in a PCR assay. Thus results from this "probe check assay" can be used as a measure of the functional performance of the probe in an assay.

Figure 12:
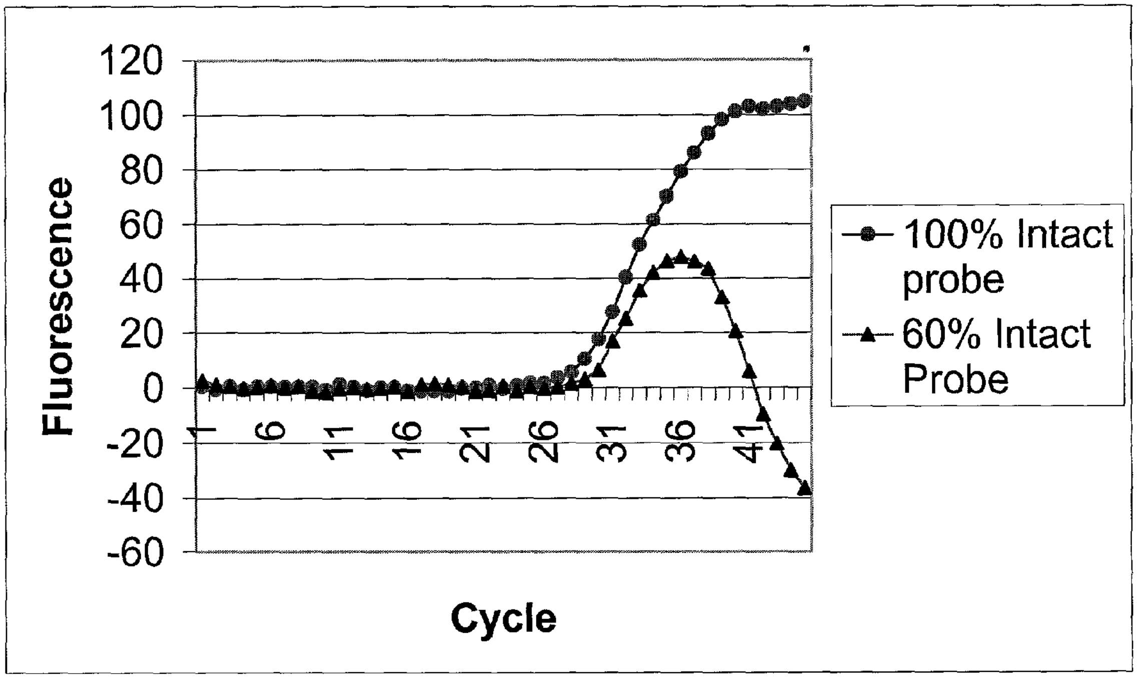
FIG. 12 illustrates the fluorescence of two different probes specific for a particular amplified sequence. Fluorescence is measured relative to the number of amplification cycles.
Figure 13:
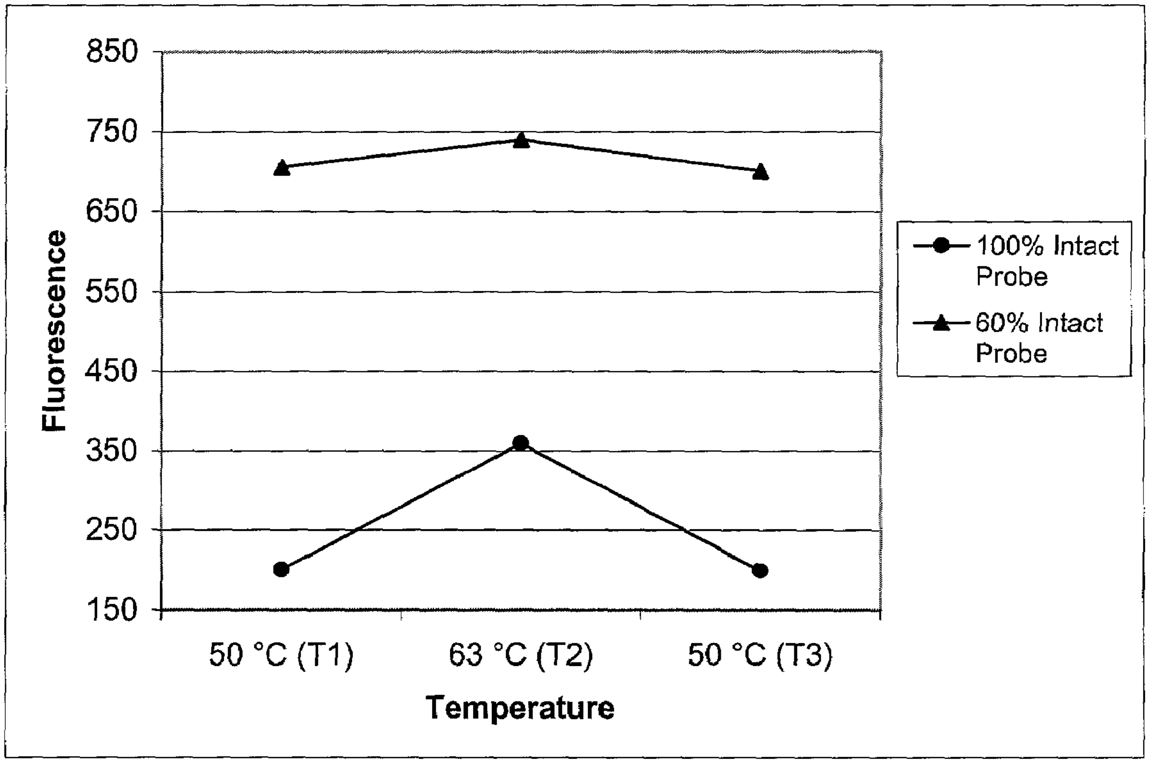
FIG. 13 illustrates the difference in 100% intact and 60% intact molecular beacon probes at different temperatures.

FIGS. 12 and 13 show the results of probe check assay and PCR results for an intact probe and a mixture of intact and cleaved probes. In both cases, the final concentration of probe was 200 nM. The fluorescence of the PCR reaction mixture was determined at 50° C. (temperature T1) and 63° C. (temperature T2) and again at 50° C. (temperature T3). See, Table 4. There is a significant difference in probe check fluorescence readings of PCR reactions mixtures that contain 100% intact and 60% intact probes (FIG. 13) and this difference can be correlated with poor PCR performance.

TABLE 4

Probe Check results for intact and partially intact Molecular Beacons probes.

| % Intact Probe | Fluorescence at T1 | Fluorescence at T2 | Fluorescence at T3 | Fluorescence T2–T1 |
|---|---|---|---|---|
| 100 | 200 | 359 | 199 | 159 |
| 60% | 705 | 740 | 700 | 35 |

Example 2

This example illustrates the determination of a threshold value based on results from mixtures of degraded and intact probes.

Mixtures of intact filly functional probe and cleaved probes were prepared and evaluated by both a Probe Check and real-time PCR assay. Probe mixtures ranged from 100% to 0% intact probe in 10% intervals (e.g., 90%, 80%, 70%, etc.). Non-functional probes in this example were probes that were cleaved in the loop sequence. Cleavage leads to an instability of the stem sequence and a subsequent increase of probe fluorescence at temperatures below the annealing temperature of the stem sequence.

Real time quantification results were obtained for a target template using mixtures of intact and cleaved probe. In addition, a probe check assay was performed for each probe mixture. For the probe check, the fluorescence of the PCR reaction mixtures were read at 2 temperatures, T1 (a temperature below the self-annealing temperature of the probe) and T2 (a temperature above the self-annealing temperature of the probe. The difference in these fluorescence readings (T2–T1) was then used as the probe check value.

Figure 14:
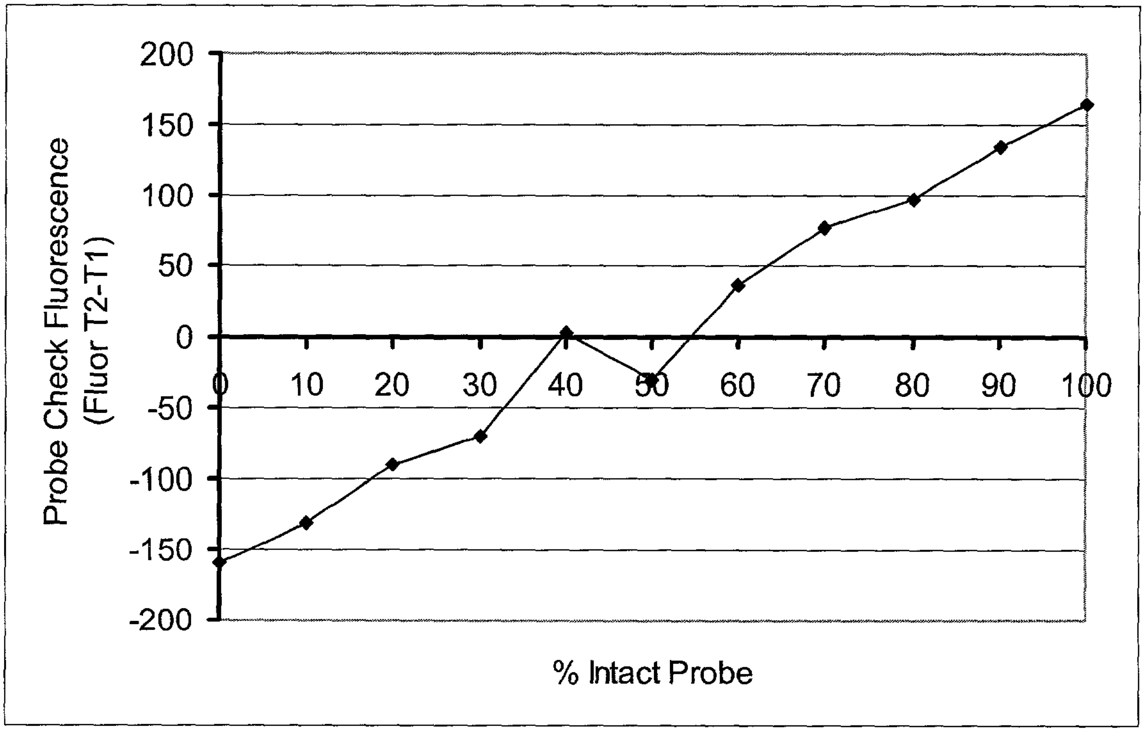
FIG. 14 illustrates the relationship between the fraction of intact molecular beacon probe in a reaction mixture and probe check reading calculated as fluorescence at T2 minus fluorescence at T1.

Probe mixtures that contained between 100 and 80% intact probe had acceptable PCR performance and had increasing fluorescence readings at around 35 cycles. Higher proportions of degraded probe in the mixture lead to poor PCR results. For example, the 70% intact probe mixture did not demonstrate significant increases in fluorescence at later cycle numbers. For mixtures with even less intact probe, fluorescence readings dropped as a function of cycle number. Based on these results a Probe Check threshold value (T2–T1) of 100 fluorescence units (FIG. 14) could be used to predict the PCR performance of a mixture of cleaved and intact probes.

Example 3

This example illustrates the utility of the probe check method for improving the precision of fluorescence readings.

To demonstrate the ability of the probe check functionality to improve the precision of optical reads for fluorescence instrumentation, and in particular for instruments such as the Smart Cycler® (Cepheid, Sunnyvale, Calif.) which contain a different fluorometer for each reaction site, PCR assays using two different instruments were performed, and the precision of the endpoint values between curve families with and without probe check normalization were compared. For the test, a PCR for the detection of Group B streptococcus was prepared, comprised of 50 mM Tris buffer, 8 mM MgCl2, 450 μg/mL of BSA, 400 nM of forward primer, 400 nM of reverse primer, 200 nM of FAM probe SagB1, 200μM dNTP mixture, 1.25 unit of Taq polymerase, and 9000 copies of GBS genomic DNA. Sixteen 25 μL Smart Cycler reaction vessels were filled and placed in the Smart Cycler®. The probe check was run just prior to PCR, first reading at 50° C. (temperature T1), then at 63° C. (temperature T2), and again at 50° C. (temperature T3), without fluorescence background subtraction. PCR was then started, first holding at 95° C. for 180 seconds and then performing 45 cycles of PCR (95° C. for 5 seconds; 56° C. for 14 seconds with optic reading; and 72° C. for 5 seconds). Eight reactions were performed in each of two different instruments, and the data was exported to an Excel spreadsheet for analysis and graphing.

Figure 15:
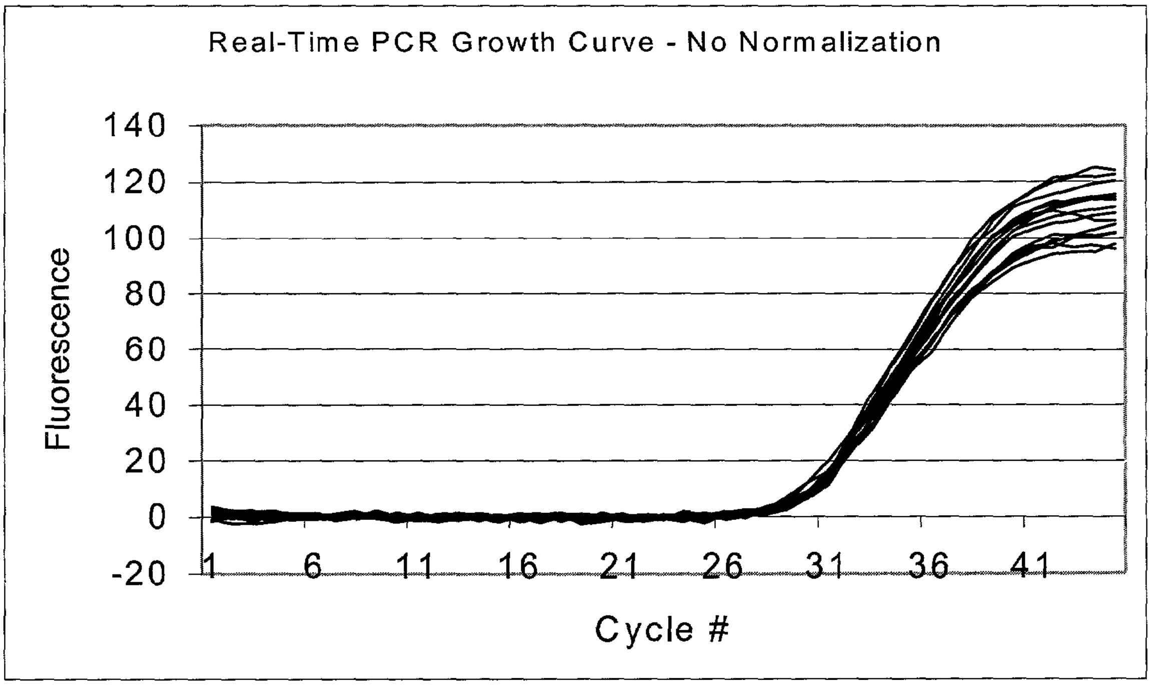
FIG. 15 illustrates the accumulation of an amplified product from a number of different reactions where the signal is not normalized.
Figure 16:
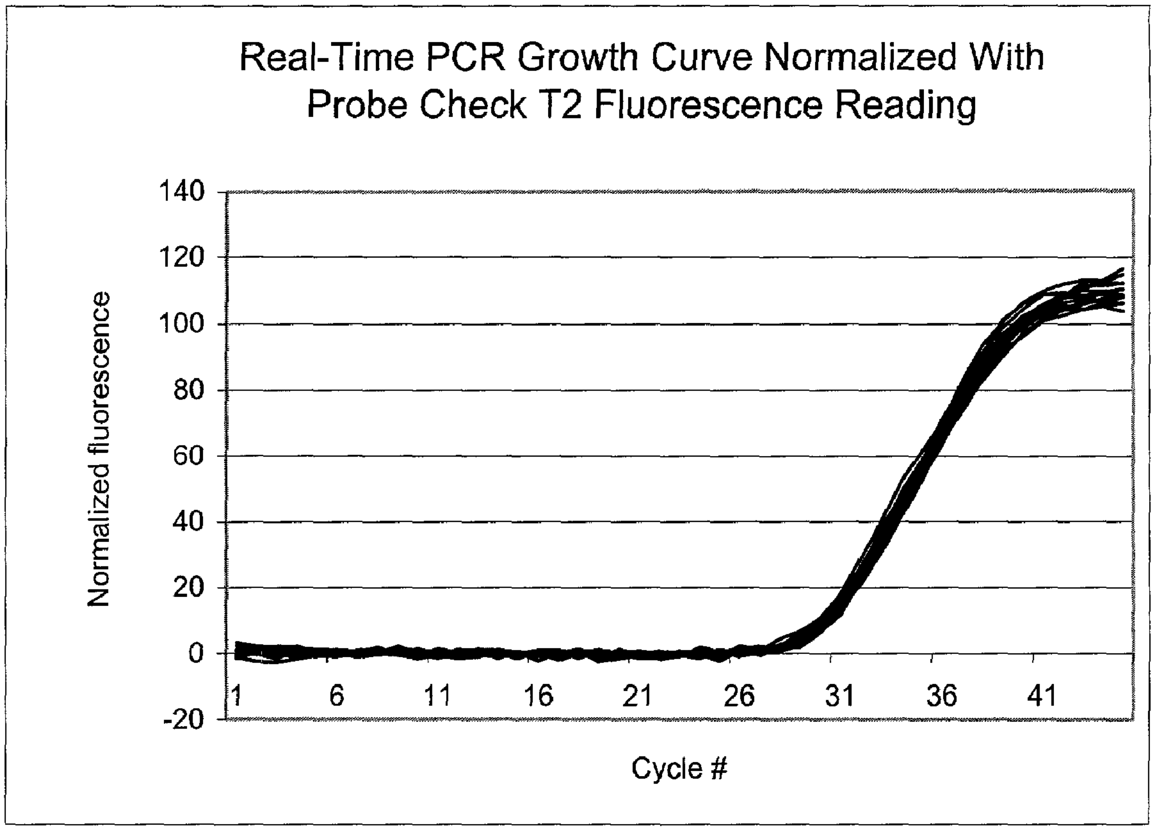
FIG. 16 illustrates the accumulation of amplified products from a number of different amplification reactions where the signal values for each amplified product are normalized to a respective probe check value.
Figure 17:
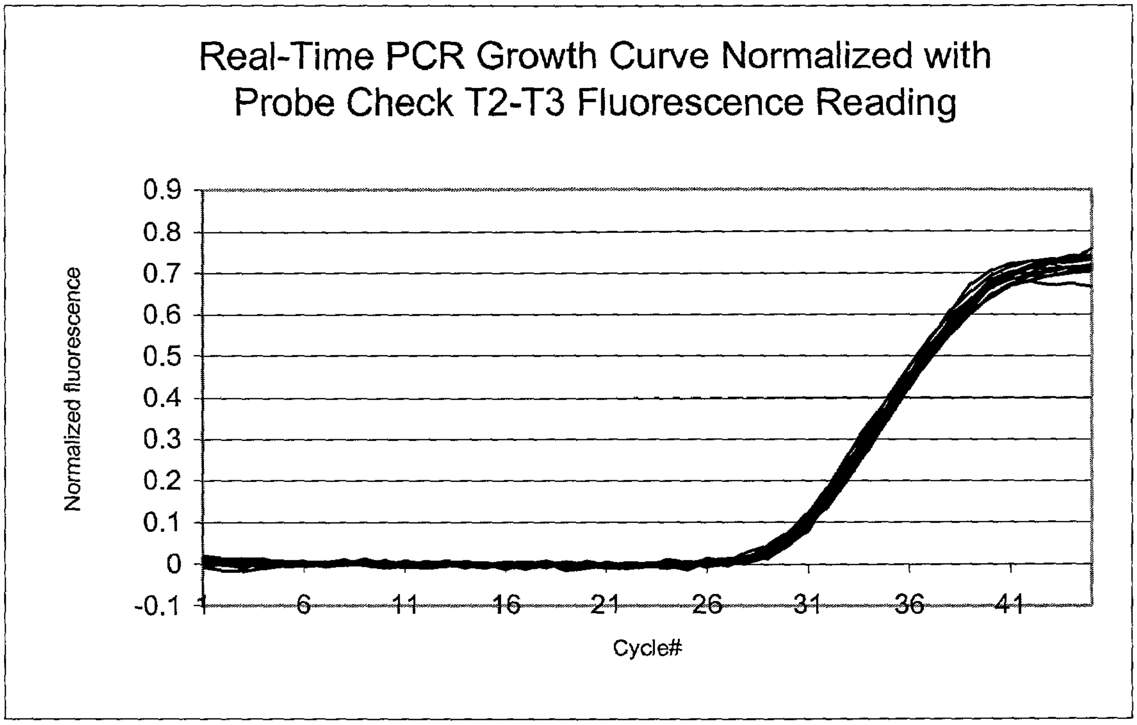
FIG. 17 illustrates the accumulation of amplified products from a number of different amplification reactions where the signal values are normalized to the difference between two probe check values measured at different temperatures.

Two graphs were prepared by analyzing the data in two ways, one without probe check normalization and one with probe check normalization. FIG. 15 shows 16 reactions without normalization and is a plot of fluorescence values with background subtracted versus cycle number. The data was then normalized using the probe check assay, i.e., each fluorescence value, with background subtracted, was either divided by the probe check temperature T2 value from its respective reaction site, or divided by the difference between the probe check signal value at temperature T2 and the probe check signal value at temperature T3. FIGS. 16 and 17 show 16 reactions with probe check normalization.

The % CV (standard deviation/mean×100) and % max–min value (maximum value–minimum value/mean×100) for each set of data was then calculated, and shown in the following table.

| Data Set | N | % CV | % (max–min) |
|---|---|---|---|
| Not normalized | 16 | 7.9 | 25.4 |
| Normalized (T2) | 16 | 3 | 11.6 |
| Normalized T2–T3 | 16 | 2.9 | 12.5 |

These data clearly show that the probe check measurement can be used to significantly improve the precision of fluorescence readings. This works by providing a compensation means for possible drifts in optical system components. For quantitative methods relying on endpoint fluorescence readings, the accuracy and precision of quantitation is improved by at least about 3-fold.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of determining if a probe is sufficiently intact to detect a target nucleic acid in a nucleic acid amplification reaction, the method comprising:

(a) providing a mixture comprising at least one probe, which probe is capable of hybridizing to the target nucleic acid;

(b) measuring a signal of the probe at one or more time points when the probe is not bound to the target nucleic acid; and (c) determining the integrity of the probe by comparing the signal of the probe at the one or more time points with at least one pre-determined threshold value indicative of the signal of the probe when the probe is intact, wherein:

the signal is fluorescence, the probe is capable of hybridizing with a target nucleic acid, the probe comprising a fluorophore and a quenching agent, wherein heating the probe causes the probe to change conformation from a first self-annealing conformation to a second conformation, thereby changing the distance between the fluorophore and the quenching agent such that the fluorescence of the fluorophore is quenched or altered in the first conformation compared to the fluorescence of the fluorophore in the second conformation, and the fluorescence of the probe is measured at a temperature equal to or below the self-annealing temperature of the probe.

2. The method of claim 1, wherein the measuring step comprises measuring the fluorescence of the probe at two or more time points selected from the group consisting of a first, second and third time point, wherein the temperature of the mixture is equal to or below the self-annealing temperature of the probe at the first time point, the temperature of the mixture is above the self-annealing temperature of the probe at the second time point, and the temperature of the mixture is equal to or below the self-annealing temperature of the probe at the third time point; and the method further comprises the step of raising the temperature of the mixture from a temperature at or below the self-annealing temperature of the probe to a temperature above the self-annealing temperature of the probe and the step of reducing the temperature of the mixture from a temperature above the self-annealing temperature of the probe to a temperature at or below the self-annealing temperature of the probe.

3. The method of claim 2, wherein the determining step comprises comparing the fluorescence of the probe at the first and third time points with at least one threshold value.

4. The method of claim 2, wherein the determining step comprises comparing the fluorescence of the probe at the second and third time points with at least one threshold value.

5. The method of claim 2, wherein the determining step comprises comparing the difference of fluorescence of the probe at the first and second time points with the threshold value.

6. The method of claim 2, wherein the determining step comprises comparing the difference of fluorescence of the probe at the second and third time points with the threshold value.

7. The method of claim 1, wherein the method comprises the step of raising the temperature of the mixture from a temperature equal to or below the self-annealing temperature of the probe to a temperature above the self-annealing temperature of the probe and the step of reducing the temperature of the mixture from a temperature above the self-annealing temperature of the probe to a temperature equal to or below the self-annealing temperature of the probe; and the measuring step comprises measuring the fluorescence of the probe after the reducing step at a temperature equal to or below the self-annealing temperature of the probe.

8. The method of claim 1, wherein the determining step comprises comparing the signal at two or more time points with two or more threshold values.

9. The method of claim 1, wherein the probe comprises an oligonucleotide labeled with a fluorophore and a quenching agent, and wherein the probe is capable of being cleaved by 5' exonuclease activity of a DNA polymerase when the probe hybridizes to an amplified nucleic acid.

10. The method of claim 1, wherein the threshold value is based on the signal of an intact probe.

11. The method of claim 1, wherein the probe is a molecular beacon.

12. The method of claim 1, wherein at least part of the method is performed during an amplification reaction, the amplification reaction comprising (a) combining in an aqueous mixture:
(i) a target probe, a first control probe and a second control probe;
(ii) a first 5' primer, a first 3' primer and a target template, the target template comprising a hybridization site for the first 5' primer, the first 3' primer and the target probe;
(iii) a first control template, the first control template comprising a hybridization site for the first 5' primer, the first 3' primer and the first control probe; and
(iv) a second 5' primer, a second 3' primer and a second control template, the second control template comprising a hybridization site for the second 5' primer, the second 3' primer, the target probe and a second control probe;
(b) performing an amplification reaction to create amplification products; and
(c) quantifying binding of the target probe, first control probe and second control probe to the amplification products.

13. The method of claim 1, wherein the method is practiced on at least two different probes in the mixture, wherein the probes are designed to hybridize to different nucleic acid sequences.

14. The method of claim 1, wherein the mixture further comprises a dye, the method further comprising measuring a signal from the dye and normalizing the signal from the probe to the signal from the dye.

15. A computer program product readable by a machine, the machine comprising at least one detection mechanism for measuring at one or more time points a signal of at least one probe for the detection of a nucleic acid sequence, and the machine comprising a temperature control system for changing the temperature of a mixture containing the probe, wherein the probe is capable of hybridizing to a target nucleic acid,
the computer program product embodying a program of instructions executable by the machine to perform the steps comprising:
(a) measuring a signal of the probe at one or more time points when the probe is not bound to the target nucleic acid; and
(b) determining if the probe is sufficiently intact to detect the target nucleic acid in a nucleic acid amplification reaction by comparing the signal of the probe at the one or more time points with at least one pre-determined threshold value indicating signal of the probe when the probe is intact; wherein:
the signal is fluorescence,
the probe comprises a fluorophore and a quenching agent, and heating the probe causes the probe to change conformation from a first self-annealing conformation to a second conformation, thereby changing the distance between the fluorophore and the quenching agent such that the fluorescence of the fluorophore is quenched or altered in the first conformation compared to the fluorescence of the fluorophore in the second conformation, and
the measuring step comprises measuring the fluorescence of the probe at a temperature equal to or below the self-annealing temperature of the probe.

16. The computer program product of claim 15, wherein the program of instructions further comprises steps of:
(a) measuring the fluorescence of the probe at two or more time points selected from the group consisting of a first, second and third time point, wherein the temperature of the mixture is equal to or below the self-annealing temperature of the probe at the first time point, the temperature of the mixture is above the self-annealing temperature of the probe at the second time point, and the temperature of the mixture is equal to or below the self-annealing temperature of the probe at the third time point; and
(b) determining the integrity of the probe by comparing the fluorescence of the probe at the two or more time points with at least one threshold value.

17. The computer program product of claim 16, wherein the program of instructions further comprises the step of raising the temperature of the mixture above the self-annealing temperature of the probe and subsequently cooling the temperature of the mixture to a temperature less than or equal to the self-annealing temperature of the probe.

18. The computer program product of claim 17, wherein the determining step comprises comparing the fluorescence of the probe at the first and third time points with at least one threshold value.

19. The computer program product of claim 17, wherein the determining step comprises comparing the fluorescence of the probe at the second and third time points with at least one threshold value.

20. The computer program product of claim 17, wherein the determining step comprises comparing the difference of fluorescence of the probe at the first and second time points with the threshold value.

21. The computer program product of claim 17, wherein the determining step comprises comparing the difference of fluorescence of the probe at the second and third time points with the threshold value.

22. The computer program product of claim 15, wherein the program of instructions further comprises steps of:
raising the temperature of the mixture from a temperature equal to or below the self-annealing temperature of the probe to a temperature above the self-annealing temperature of the probe;
reducing the temperature of the mixture from a temperature above the self-annealing temperature of the probe to a temperature equal to or below the self-annealing temperature of the probe; and
measuring the fluorescence of the probe after the reducing step at a temperature equal to or below the self-annealing temperature of the probe.

23. The computer program product of claim 15, wherein the threshold value is based on the signal of an intact probe.

24. The computer program product of claim 15, wherein the program of instructions comprises determining the integrity of at least two different probes in the mixture, the probes being capable of binding to different nucleic acid sequences.

25. The computer program product of claim 15, wherein the program of instructions further comprises steps of:
measuring a signal from a dye and;
normalizing the signal from the probe to the signal from the dye.

26. A method of determining if a probe is sufficiently intact to detect a target nucleic acid in a nucleic acid amplification reaction, the method comprising:
(a) providing a mixture comprising at least one probe, which probe is capable of hybridizing to the target nucleic acid;
(b) measuring a signal of the probe at one or more time points when the probe is not bound to the target nucleic acid; and
(c) determining the integrity of the probe by comparing the signal of the probe at the one or more time points with at least one pre-determined threshold value indicative of the signal of the probe when the probe is intact, wherein:

the signal is fluorescence, the probe is capable of hybridizing with a target nucleic acid, the probe comprising a fluorophore and a quenching agent, wherein heating the probe causes the probe to change conformation from a first self-annealing conformation to a second conformation, thereby changing the distance between the fluorophore and the quenching agent such that the fluorescence of the fluorophore is quenched or altered in the first conformation compared to the fluorescence of the fluorophore in the second conformation, and the fluorescence of the probe is measured at a temperature above the self-annealing temperature of the probe.

27. The method of claim 26, wherein the measuring step comprises measuring the fluorescence of the probe at two or more time points selected from the group consisting of a first, second and third time point, wherein the temperature of the mixture is equal to or below the self-annealing temperature of the probe at the first time point, the temperature of the mixture is above the self-annealing temperature of the probe at the second time point, and the temperature of the mixture is equal to or below the self-annealing temperature of the probe at the third time point; and the method further comprises the step of raising the temperature of the mixture from a temperature at or below the self-annealing temperature of the probe to a temperature above the self-annealing temperature of the probe and the step of reducing the temperature of the mixture from a temperature above the self-annealing temperature of the probe to a temperature at or below the self-annealing temperature of the probe.

28. The method of claim 27, wherein the determining step comprises comparing the fluorescence of the probe at the first and third time points with at least one threshold value.

29. The method of claim 27, wherein the determining step comprises comparing the fluorescence of the probe at the second and third time points with at least one threshold value.

30. The method of claim 27, wherein the determining step comprises comparing the difference of fluorescence of the probe at the first and second time points with the threshold value.

31. The method of claim 27, wherein the determining step comprises comparing the difference of fluorescence of the probe at the second and third time points with the threshold value.

32. The method of claim 26, wherein the method comprises the step of raising the temperature of the mixture from a temperature equal to or below the self-annealing temperature of the probe to a temperature above the self-annealing temperature of the probe; and the measuring step comprises measuring the fluorescence of the probe after the raising step at a temperature above the self-annealing temperature of the probe.

33. The method of claim 32, wherein the measuring step further comprises measuring the fluorescence of the probe at a temperature equal to or below the self-annealing temperature of the probe prior to the raising step.

34. The method of claim 26, wherein the determining step comprises comparing the signal at two or more time points with two or more threshold values.

35. The method of claim 26, wherein the probe comprises an oligonucleotide labeled with a fluorophore and a quenching agent, and wherein the probe is capable of being cleaved by 5' exonuclease activity of a DNA polymerase when the probe hybridizes to an amplified nucleic acid.

36. The method of claim 26, wherein the threshold value is based on the signal of an intact probe.

37. The method of claim 26, wherein the probe is a molecular beacon.

38. The method of claim 26, wherein at least part of the method is performed during an amplification reaction, the amplification reaction comprising (a) combining in an aqueous mixture:

(i) a target probe, a first control probe and a second control probe;

(ii) a first 5' primer, a first 3' primer and a target template, the target template comprising a hybridization site for the first 5' primer, the first 3' primer and the target probe;

(iii) a first control template, the first control template comprising a hybridization site for the first 5' primer, the first 3' primer and the first control probe; and (iv) a second 5' primer, a second 3' primer and a second control template, the second control template comprising a hybridization site for the second 5' primer, the second 3' primer, the target probe and a second control probe;

(b) performing an amplification reaction to create amplification products; and (c) quantifying binding of the target probe, first control probe and second control probe to the amplification products.

39. The method of claim 26, wherein the method is practiced on at least two different probes in the mixture, wherein the probes are designed to hybridize to different nucleic acid sequences.

40. The method of claim 26, wherein the mixture further comprises a dye, the method further comprising measuring a signal from the dye and normalizing the signal from the probe to the signal from the dye.

41. A method of determining if a probe is sufficiently intact to detect a target nucleic acid in a nucleic acid amplification reaction, the method comprising:

(a) providing a mixture comprising at least one probe, which probe is capable of hybridizing to the target nucleic acid;

(b) measuring a signal of the probe at one or more time points when the probe is not bound to the target nucleic acid; and (c) determining the integrity of the probe by comparing the signal of the probe at the one or more time points with at least one pre-determined threshold value indicative of the signal of the probe when the probe is intact, wherein:

the signal is fluorescence, the probe is capable of hybridizing with a target nucleic acid, the probe comprising a fluorophore and a quenching agent, wherein heating the probe causes the probe to change conformation from a first self-annealing conformation to a second conformation, thereby changing the distance between the fluorophore and the quenching agent such that the fluorescence of the fluorophore is quenched or altered in the first conformation compared to the fluorescence of the fluorophore in the second conformation, the method comprises the step of raising the temperature of the mixture from a temperature equal to or below the self-annealing temperature of the probe to a temperature above the self-annealing temperature of the probe and the step of reducing the temperature of the mixture from a temperature above the self-annealing temperature of the probe to a temperature equal to or below the self-annealing temperature of the probe; and the measuring step comprises measuring the fluorescence of the probe after the reducing step at a temperature equal to or below the self-annealing temperature of the probe.

42. A method of determining if a probe is sufficiently intact to detect a target nucleic acid in a nucleic acid amplification reaction, the method comprising:

(a) providing a mixture comprising at least one probe, which probe is capable of hybridizing to the target nucleic acid;

(b) measuring a signal of the probe at one or more time points when the probe is not bound to the target nucleic acid; and (c) determining the integrity of the probe by comparing the signal of the probe at the one or more time points with at least one pre-determined threshold value indicative of the signal of the probe when the probe is intact, wherein:

the signal is fluorescence, the probe is capable of hybridizing with a target nucleic acid, the probe comprising a fluorophore and a quenching agent, wherein heating the probe causes the probe to change conformation from a first self-annealing conformation to a second conformation, thereby changing the distance between the fluorophore and the quenching agent such that the fluorescence of the fluorophore is quenched or altered in the first conformation compared to the fluorescence of the fluorophore in the second conformation, the method comprises the step of raising the temperature of the mixture from a temperature equal to or below the self-annealing temperature of the probe to a temperature above the self-annealing temperature of the probe; and the measuring step comprises measuring the fluorescence of the probe after the raising step at a temperature above the self-annealing temperature of the probe.

43. A method of determining if a probe is sufficiently intact to detect a target nucleic acid in a nucleic acid amplification reaction, the method comprising:

(a) providing a mixture comprising at least one probe, which probe is capable of hybridizing to the target nucleic acid;

(b) measuring a signal of the probe at one or more time points when the probe is not bound to the target nucleic acid; and (c) determining the integrity of the probe by comparing the signal of the probe at the one or more time points with at least one pre-determined threshold value indicative of the signal of the probe when the probe is intact, wherein:

the determining step comprises comparing the signal at two or more time points with two or more threshold values.

44. The method of claim 43, wherein the signal is fluorescence.

45. The method of claim 44, wherein the probe is capable of hybridizing with a target nucleic acid, the probe comprising a fluorophore and a quenching agent, wherein heating the probe causes the probe to change conformation from a first self-annealing conformation to a second conformation, thereby changing the distance between the fluorophore and the quenching agent such that the fluorescence of the fluorophore is quenched or altered in the first conformation compared to the fluorescence of the fluorophore in the second conformation.

46. The method of claim 45, wherein the fluorescence of the probe is measured at a temperature equal to or below the self-annealing temperature of the probe.

47. The method of claim 45, wherein the fluorescence of the probe is measured at a temperature above the self-annealing temperature of the probe.

48. The method of claim 45, wherein the measuring step comprises measuring the fluorescence of the probe at two or more time points selected from the group consisting of a first, second and third time point, wherein the temperature of the mixture is equal to or below the self-annealing temperature of the probe at the first time point, the temperature of the mixture is above the self-annealing temperature of the probe at the second time point, and the temperature of the mixture is equal to or below the self-annealing temperature of the probe at the third time point; and the method further comprises the step of raising the temperature of the mixture from a temperature at or below the self-annealing temperature of the probe to a temperature above the self-annealing temperature of the probe and the step of reducing the temperature of the mixture from a temperature above the self-annealing temperature of the probe to a temperature at or below the self-annealing temperature of the probe.

49. The method of claim 48, wherein the determining step comprises comparing the fluorescence of the probe at the first and third time points with at least one threshold value.

50. The method of claim 48, wherein the determining step comprises comparing the fluorescence of the probe at the second and third time points with at least one threshold value.

51. The method of claim 48, wherein the determining step comprises comparing the difference of fluorescence of the probe at the first and second time points with the threshold value.

52. The method of claim 48, wherein the determining step comprises comparing the difference of fluorescence of the probe at the second and third time points with the threshold value.

53. The method of claim 45, wherein the method comprises the step of raising the temperature of the mixture from a temperature equal to or below the self-annealing temperature of the probe to a temperature above the self-annealing temperature of the probe and the step of reducing the temperature of the mixture from a temperature above the self-annealing temperature of the probe to a temperature equal to or below the self-annealing temperature of the probe; and the measuring step comprises measuring the fluorescence of the probe after the reducing step at a temperature equal to or below the self-annealing temperature of the probe.

54. The method of claim 45, wherein the method comprises the step of raising the temperature of the mixture from a temperature equal to or below the self-annealing temperature of the probe to a temperature above the self-annealing temperature of the probe; and the measuring step comprises measuring the fluorescence of the probe after the raising step at a temperature above the self-annealing temperature of the probe.

55. The method of claim 54, wherein the measuring step further comprises measuring the fluorescence of the probe at a temperature equal to or below the self-annealing temperature of the probe prior to the raising step.

56. The method of claim 44, wherein the probe comprises an oligonucleotide labeled with a fluorophore and a quenching agent, and wherein the probe is capable of being cleaved by 5' exonuclease activity of a DNA polymerase when the probe hybridizes to an amplified nucleic acid.

57. The method of claim 43, wherein the threshold value is based on the signal of an intact probe.

58. The method of claim 45, wherein the probe is a molecular beacon.

59. The method of claim 43, wherein at least part of the method is performed during an amplification reaction, the amplification reaction comprising (a) combining in an aqueous mixture:

(i)a target probe, a first control probe and a second control probe;

(ii)a first 5' primer, a first 3' primer and a target template, the target template comprising a hybridization site for the first 5' primer, the first 3' primer and the target probe;

(iii) a first control template, the first control template comprising a hybridization site for the first 5' primer, the first 3' primer and the first control probe; and (iv) a second 5' primer, a second 3' primer and a second control template, the second control template comprising a hybridization site for the second 5' primer, the second 3' primer, the target probe and a second control probe;

(b) performing an amplification reaction to create amplification products; and (c) quantifying binding of the target probe, first control probe and second control probe to the amplification products.

60. The method of claim 43, wherein the method is practiced on at least two different probes in the mixture, wherein the probes are designed to hybridize to different nucleic acid sequences.

61. The method of claim 43, wherein the mixture further comprises a dye, the method further comprising measuring a signal from the dye and normalizing the signal from the probe to the signal from the dye.

62. A method of determining if at least two different probes designed to hybridize to different nucleic acid sequences are sufficiently intact to detect their respective target nucleic acids in a nucleic acid amplification reaction, the method comprising:

(a) providing a mixture comprising at least two probes, which probes are capable of hybridizing to their respective target nucleic acids;

(b) measuring signals of the probes at one or more time points when the probes are not bound to their respective target nucleic acids; and (c) determining the integrity of the probes by comparing the signals of the probes at the one or more time points with at least one pre-determined threshold value indicative of the signal of the probes when the probes are intact.

63. The method of claim 62, wherein the signal is fluorescence.

64. The method of claim 63, wherein the probes are capable of hybridizing with a target nucleic acid, each probe comprising a fluorophore and a quenching agent, wherein heating the probes causes the probes to change conformation from a first self-annealing conformation to a second conformation, thereby changing the distance between the fluorophore and the quenching agent such that the fluorescence of the fluorophore is quenched or altered in the first conformation compared to the fluorescence of the fluorophore in the second conformation.

65. The method of claim 64, wherein the fluorescence of the probes are measured at a temperature equal to or below the self-annealing temperature of the probes.

66. The method of claim 64, wherein the fluorescence of the probes is measured at a temperature above the self-annealing temperature of the probes.

67. The method of claim 64, wherein the measuring step comprises measuring the fluorescence of the probes at two or more time points selected from the group consisting of a first, second and third time point, wherein the temperature of the mixture is equal to or below the self-annealing temperature of the probes at the first time point, the temperature of the mixture is above the self-annealing temperature of the probes at the second time point, and the temperature of the mixture is equal to or below the self-annealing temperature of the probes at the third time point; and the method further comprises the step of raising the temperature of the mixture from a temperature at or below the self-annealing temperature of the probes to a temperature above the self-annealing temperature of the probes and the step of reducing the temperature of the mixture from a temperature above the self-annealing temperature of the probes to a temperature at or below the self-annealing temperature of the probes.

68. The method of claim 67, wherein the determining step comprises comparing the fluorescence of the probes at the first and third time points with at least one threshold value.

69. The method of claim 67, wherein the determining step comprises comparing the fluorescence of the probes at the second and third time points with at least one threshold value.

70. The method of claim 67, wherein the determining step comprises comparing the difference of fluorescence of the probes at the first and second time points with the threshold value.

71. The method of claim 67, wherein the determining step comprises comparing the difference of fluorescence of the probes at the second and third time points with the threshold value.

72. The method of claim 64, wherein the method comprises the step of raising the temperature of the mixture from a temperature equal to or below the self-annealing temperature of the probes to a temperature above the self-annealing temperature of the probes and the step of reducing the temperature of the mixture from a temperature above the self-annealing temperature of the probes to a temperature equal to or below the self-annealing temperature of the probes; and the measuring step comprises measuring the fluorescence of the probes after the reducing step at a temperature equal to or below the self-annealing temperature of the probes.

73. The method of claim 64, wherein the method comprises the step of raising the temperature of the mixture from a temperature equal to or below the self-annealing temperature of the probes to a temperature above the self-annealing temperature of the probes; and the measuring step comprises measuring the fluorescence of the probes after the raising step at a temperature above the self-annealing temperature of the probes.

74. The method of claim 73, wherein the measuring step further comprises measuring the fluorescence of the probes at a temperature equal to or below the self-annealing temperature of the probes prior to the raising step.

75. The method of claim 62, wherein the determining step comprises comparing the signal at two or more time points with two or more threshold values.

76. The method of claim 63, wherein the probes comprises an oligonucleotide labeled with a fluorophore and a quenching agent, and wherein the probes are capable of being cleaved by 5' exonuclease activity of a DNA polymerase when the probes hybridize to an amplified nucleic acid.

77. The method of claim 62, wherein the threshold value is based on the signal of an intact probes.

78. The method of claim 64, wherein the probes are molecular beacons.

79. The method of claim 62, wherein at least part of the method is performed during an amplification reaction, the amplification reaction comprising (a) combining in an aqueous mixture:

(i) a target probe, a first control probe and a second control probe;

(ii) a first 5' primer, a first 3' primer and a target template, the target template comprising a hybridization site for the first 5' primer, the first 3' primer and the target probe;

(iii) a first control template, the first control template comprising a hybridization site for the first 5' primer, the first 3' primer and the first control probe; and (iv) a second 5' primer, a second 3' primer and a second control template, the second control template comprising a hybridization site for the second 5' primer, the second 3' primer, the target probe and a second control probe;

(b) performing an amplification reaction to create amplification products; and (c) quantifying binding of the target probe, first control probe and second control probe to the amplification products.

80. The method of claim 62, wherein the mixture further comprises a dye, the method further comprising measuring a signal from the dye and normalizing the signal from the probes to the signal from the dye.

81. A computer program product readable by a machine, the machine comprising at least one detection mechanism for measuring at one or more time points a signal of at least one probe for the detection of a nucleic acid sequence, and the machine comprising a temperature control system for changing the temperature of a mixture containing the probe, wherein the probe is capable of hybridizing to a target nucleic acid, the computer program product embodying a program of instructions executable by the machine to perform the steps comprising:

(a) measuring a signal of the probe at one or more time points when the probe is not bound to the target nucleic acid; and (b) determining if the probe is sufficiently intact to detect the target nucleic acid in a nucleic acid amplification reaction by comparing the signal of the probe at the one or more time points with at least one pre-determined threshold value indicating signal of the probe when the probe is intact; wherein:

the signal is fluorescence, the probe comprises a fluorophore and a quenching agent, and heating the probe causes the probe to change conformation from a first self-annealing conformation to a second conformation, thereby changing the distance between the fluorophore and the quenching agent such that the fluorescence of the fluorophore is quenched or altered in the first conformation compared to the fluorescence of the fluorophore in the second conformation, and the measuring step comprises measuring the fluorescence of the probe at a temperature above the self-annealing temperature of the probe.

82. The computer program product of claim 81, wherein the program of instructions further comprises steps of:

(a) measuring the fluorescence of the probe at two or more time points selected from the group consisting of a first, second and third time point, wherein the temperature of the mixture is equal to or below the self-annealing temperature of the probe at the first time point, the temperature of the mixture is above the self-annealing temperature of the probe at the second time point, and the temperature of the mixture is equal to or below the self-annealing temperature of the probe at the third time point; and (b) determining the integrity of the probe by comparing the fluorescence of the probe at the two or more time points with at least one threshold value.

83. The computer program product of claim 81, wherein the program of instructions further comprises the steps of:

raising the temperature of the mixture from a temperature equal to or below the self-annealing temperature of the probe to a temperature above the self-annealing temperature of the probe; and measuring the fluorescence of the probe at a temperature above the self-annealing temperature of the probe.

84. The computer program product of claim 83, wherein the program of instructions further comprises the step of measuring the fluorescence of the probe at a temperature equal to or below the self-annealing temperature of the probe prior to the raising step.

85. The computer program product of claim 81, wherein the threshold value is based on the signal of an intact probe.

86. The computer program product of claim 81, wherein the program of instructions comprises determining the integrity of at least two different probes in the mixture, the probes being capable of binding to different nucleic acid sequences.

87. The computer program product of claim 81, wherein the program of instructions further comprises steps of:

measuring a signal from a dye and;

normalizing the signal from the probe to the signal from the dye.

88. A computer program product readable by a machine, the machine comprising at least one detection mechanism for measuring at one or more time points a signal of at least one probe for the detection of a nucleic acid sequence, and the machine comprising a temperature control system for changing the temperature of a mixture containing the probe, wherein the probe is capable of hybridizing to a target nucleic acid, the computer program product embodying a program of instructions executable by the machine to perform the steps comprising:

(a) measuring a signal of the probe at one or more time points when the probe is not bound to the target nucleic acid; and (b) determining if the probe is sufficiently intact to detect the target nucleic acid in a nucleic acid amplification reaction by comparing the signal of the probe at the one or more time points with at least one pre-determined threshold value indicating signal of the probe when the probe is intact; wherein:

the signal is fluorescence, the probe comprises a fluorophore and a quenching agent, and heating the probe causes the probe to change conformation from a first self-annealing conformation to a second conformation, thereby changing the distance between the fluorophore and the quenching agent such that the fluorescence of the fluorophore is quenched or altered in the first conformation compared to the fluorescence of the fluorophore in the second conformation, and wherein the program of instructions further comprises steps of:

raising the temperature of the mixture from a temperature equal to or below the self-annealing temperature of the probe to a temperature above the self-annealing temperature of the probe;

reducing the temperature of the mixture from a temperature above the self-annealing temperature of the probe to a temperature equal to or below the self-annealing temperature of the probe; and measuring the fluorescence of the probe after the reducing step at a temperature equal to or below the self-annealing temperature of the probe.

89. A computer program product readable by a machine, the machine comprising at least one detection mechanism for measuring at one or more time points a signal of at least one probe for the detection of a nucleic acid sequence, and the machine comprising a temperature control system for changing the temperature of a mixture containing the probe, wherein the probe is capable of hybridizing to a target nucleic acid, the computer program product embodying a program of instructions executable by the machine to perform the steps comprising:

(a) measuring a signal of the probe at one or more time points when the probe is not bound to the target nucleic acid; and (b) determining if the probe is sufficiently intact to detect the target nucleic acid in a nucleic acid amplification reaction by comparing the signal of the probe at the one or more time points with at least one pre-determined threshold value indicating signal of the probe when the probe is intact; wherein:

the signal is fluorescence, the probe comprises a fluorophore and a quenching agent, and heating the probe causes the probe to change conformation from a first self-annealing conformation to a second conformation, thereby changing the distance between the fluorophore and the quenching agent such that the fluorescence of the fluorophore is quenched or altered in the first conformation compared to the fluorescence of the fluorophore in the second conformation, and wherein the program of instructions further comprises steps of:

raising the temperature of the mixture from a temperature equal to or below the self-annealing temperature of the probe to a temperature above the self-annealing temperature of the probe; and measuring the fluorescence of the probe at a temperature above the self-annealing temperature of the probe.

* * * * *